United States Patent
Borlaug et al.

(10) Patent No.: US 8,080,001 B2
(45) Date of Patent: Dec. 20, 2011

(54) FLUID CONNECTION ASSEMBLY WITH LOCKING MECHANISM

(75) Inventors: Tom Borlaug, Prior Lake, MN (US); Marty Hieb, St. Louis Park, MN (US); Khoi Le, Chanhassen, MN (US); Chris Lins, Crystal, MN (US); Steven Paul Plager, Eden Prairie, MN (US); Darryl Wrolson, Waconia, MN (US); Nathaniel R. Hallee, Minneapolis, MN (US); Paul Pilosi, Minnetonka, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 109 days.

(21) Appl. No.: 12/324,512

(22) Filed: Nov. 26, 2008

(65) Prior Publication Data

US 2010/0130922 A1     May 27, 2010

(51) Int. Cl.
*A61M 39/00* (2006.01)
*A61M 31/00* (2006.01)
(52) U.S. Cl. ..................... 604/533; 604/93.01
(58) Field of Classification Search ............... 604/93.01, 604/533, 80, 94.01, 240, 242, 535
See application file for complete search history.

(56) References Cited

U.S. PATENT DOCUMENTS

| | | | |
|---|---|---|---|
| 5,573,515 A | 11/1996 | Wilson et al. | |
| 6,866,654 B2 * | 3/2005 | Callan et al. | 604/247 |
| 2005/0101939 A1 | 5/2005 | Mitchell | |

FOREIGN PATENT DOCUMENTS

| | | |
|---|---|---|
| EP | 0 340 427 A2 | 11/1989 |
| WO | WO 83/00812 | 3/1983 |
| WO | WO 2007/033103 A1 | 3/2007 |
| WO | WO 2007/062315 A3 | 5/2007 |
| WO | WO 2007/089201 A1 | 8/2007 |
| WO | WO2008/069052 A1 | 6/2008 |

OTHER PUBLICATIONS

Notification of Transmittal of the International Search Report and the Written Opinion of the International Searching Authority, or the Declaration from corresponding PCT Application No. PCT/US2009/065450 mailed Feb. 25, 2010 (12 pages).
"ACIST CVi Contrast Delivery System User Manual", ACIST Medical Systems, Inc., Nov. 2005, (91 pages).

(Continued)

*Primary Examiner* — Nicholas Lucchesi
*Assistant Examiner* — Brooke Matney
(74) *Attorney, Agent, or Firm* — Shumaker & Sieffert, P.A.

(57) ABSTRACT

In general, this disclosure relates to techniques for implementation and use of a fluid connection assembly, having a locking mechanism, which may be connected to a medical fluid injection device. An example fluid connection assembly includes at least one fluid connector, a mating mechanism coupled to the at least one fluid connector and configured to connect the at least one fluid connector to a medical fluid injection device, and a locking mechanism coupled to the mating mechanism and movable into a locked position or an unlocked position. In this example, the fluid connection assembly becomes affirmatively coupled with the medical fluid injection device when the locking mechanism is in the locked position, and the fluid connection assembly becomes removably decoupled from the medical fluid injection device when the locking mechanism is in the unlocked position.

21 Claims, 18 Drawing Sheets

OTHER PUBLICATIONS

U.S. Appl. No. 12/261,713, filed Oct. 30, 2008, entitled "Automatically Supplying a Pressurizing Unit of a Medical Injection Device With Fluid".

U.S. Appl. No. 12/261,415, filed Oct. 30, 2008, entitled "Mating Mechanism for a Pressurizing Unit and Corresponding Sleeve in a Medical Fluid Injection Device".

U.S. Appl. No. 12/261,786, filed Oct. 30, 2008, entitled "Pinch Valve Mechanism for a Medical Fluid Injection Device".

International Preliminary Report on Patentability from international application No. PCT/US2009/065450, dated Jun. 9, 2011, 7 pp.

* cited by examiner

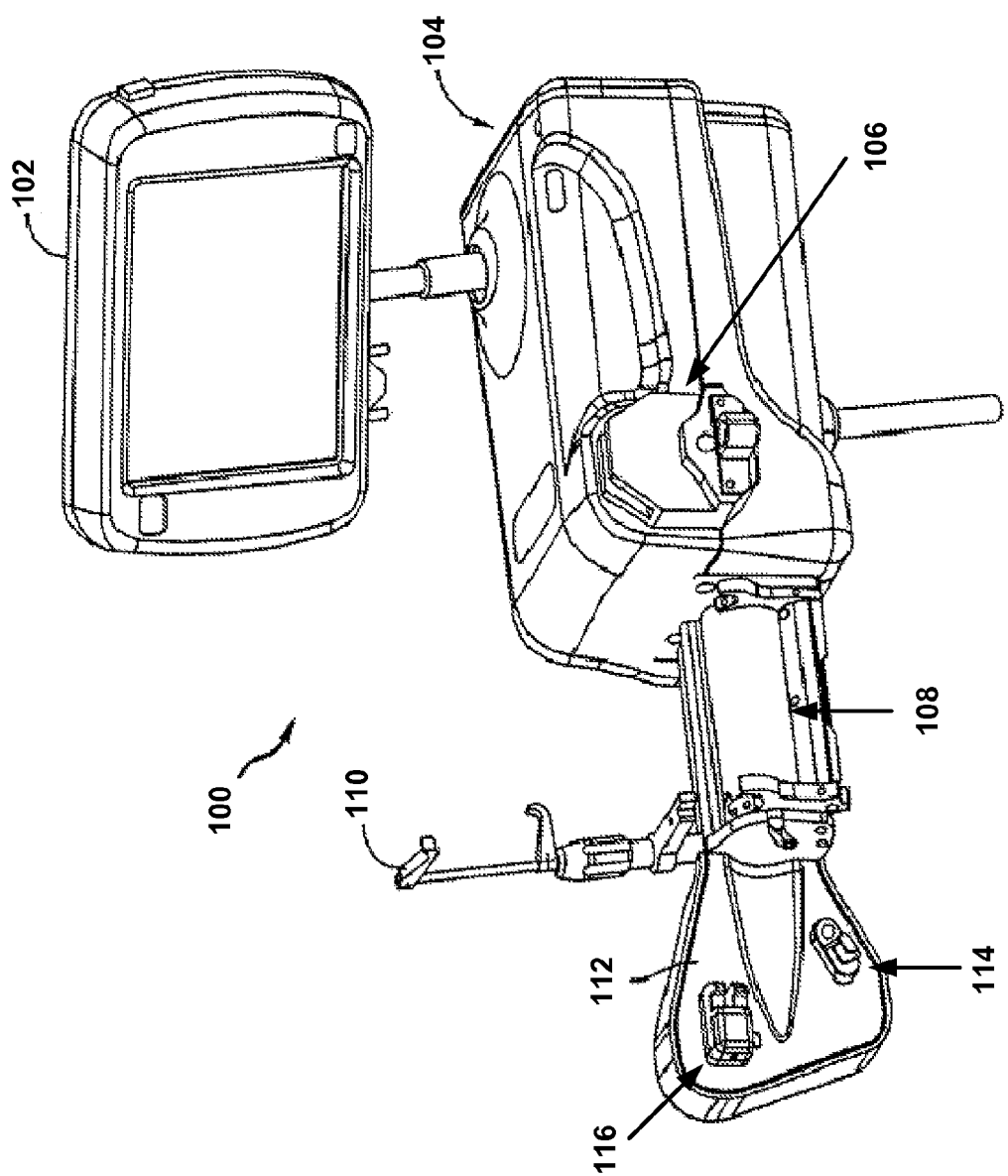

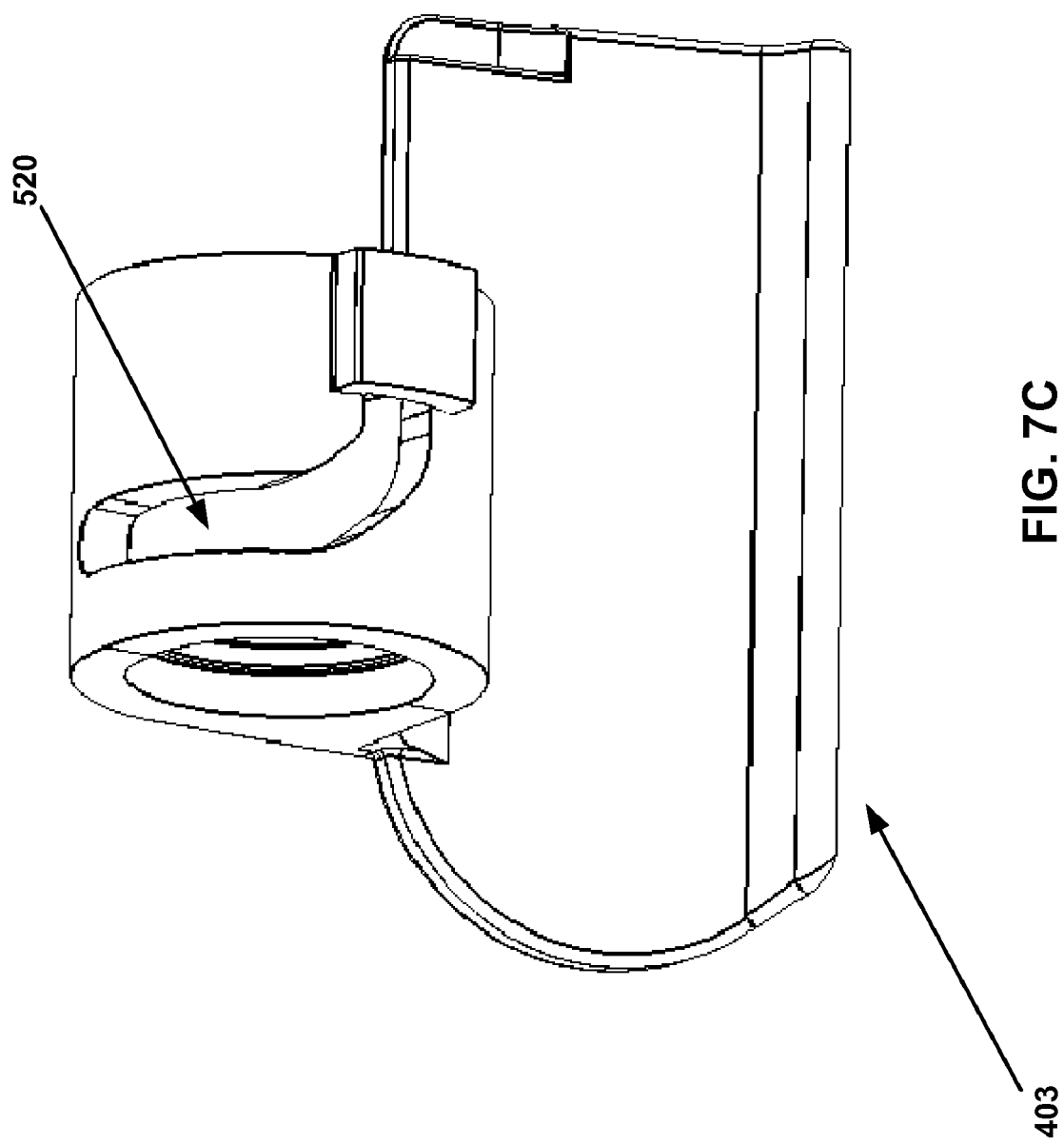

FLUID CONNECTION ASSEMBLY WITH LOCKING MECHANISM

TECHNICAL FIELD

This disclosure generally relates to the connection of components to a medical fluid injection device.

BACKGROUND

Medical fluid injection devices are typically used to inject medical fluid into a patient. These devices often include one or more reservoirs to hold the medical fluid, and one or more pressurizing units to inject the medical fluid into the patient. For example, a contrast media powered injection device may include a reservoir containing contrast media and a syringe that is used to inject the contrast media into the patient. The contrast media injection device may be used during certain medical procedures, such as an angiographic or computed tomography (CT) procedure.

Many medical fluid injection devices include one or more syringes to inject fluid. A syringe has a chamber for holding the fluid and a plunger that is moveable within the chamber. The fluid is typically drawn into the chamber from a fluid reservoir when the plunger is moved in a first direction. The fluid is then expelled from the chamber and into the patient when the plunger is moved in a second, opposite direction. The fluid is delivered at a rate that may be determined by a speed of movement of the plunger.

In many cases, fluid may be injected from a medical fluid injection device into a patient via a patient line, or tubing kit, that is connected to the injection device. In certain cases, the patient line may comprise a disposable component. For example, at the beginning of an injection procedure, a clinician may connect a sterilized patient line to the injection device. Upon completion of the injection procedure, the clinician may then disconnect the patient line from the injection device, and subsequently dispose of the patient line. The clinician may then use a new patient line, or tubing kit, for a subsequent injection procedure.

SUMMARY

In general, this disclosure relates to techniques for implementation and use of a fluid connection assembly, having a locking mechanism, which may be connected to a medical fluid injection device. The fluid connection assembly may comprise a sterilized, disposable component that may be connected to a non-sterilized injection device. In some cases, a clinician may use a one-handed manual insertion procedure to connect the fluid connection assembly, which may be part of a patient line, to the injection device. In these cases, the clinician may be able to maintain sterility while making this connection.

In one embodiment, an example fluid connection assembly includes at least one fluid connector, a mating mechanism coupled to the at least one fluid connector and configured to connect the at least one fluid connector to a medical fluid injection device, and a locking mechanism coupled to the mating mechanism and movable into a locked position or an unlocked position. The fluid connection assembly becomes affirmatively coupled to the medical fluid injection device when the locking mechanism is in the locked position. The fluid connection assembly becomes removably decoupled from the medical fluid injection device when the locking mechanism is in the unlocked position.

In one embodiment, an example method includes connecting at least one fluid connector of a fluid connection assembly to a medical fluid injection device, moving a locking mechanism of the fluid connection assembly into a locked position to affirmatively couple the fluid connection assembly to the medical fluid injection device, and moving the locking mechanism of the fluid connection assembly into an unlocked position to removably decouple the fluid connection assembly from the medical fluid injection device.

In one embodiment, an example fluid connection assembly includes a connecting means for connecting the fluid connection assembly to a medical fluid injection device, a locking means for affirmatively coupling the fluid connection assembly with the medical fluid injection device, and an unlocking means for removably decoupling the fluid connection assembly from the medical fluid injection device.

The details of one or more embodiments are set forth in the accompanying drawings and the description below. Other features, objects, and advantages will be apparent from the description and drawings, and from the claims.

BRIEF DESCRIPTION OF DRAWINGS

FIG. 1A is a perspective diagram of one embodiment of a powered medical fluid injection device that may be connected to a fluid connection assembly.

FIGS. 7A-7C are perspective diagrams of a locking mechanism included in the fluid connection assembly shown in FIGS. 5A-5D, according to one embodiment.

DETAILED DESCRIPTION

FIG. 1A is a perspective diagram of one embodiment of a powered medical fluid injection device 100 that may be connected to a fluid connection assembly. In the embodiment of FIG. 1A, the pressurizing unit within sleeve 108 is a syringe. In other embodiments, other forms of pressurizing units may be used, including other types of positive displacement pumps. Device 100 is, in some embodiments, used to inject medical fluid, such as contrast media or saline, into a patient during a medical procedure, such as an angiographic or computed tomography (CT) procedure.

Figure 3:
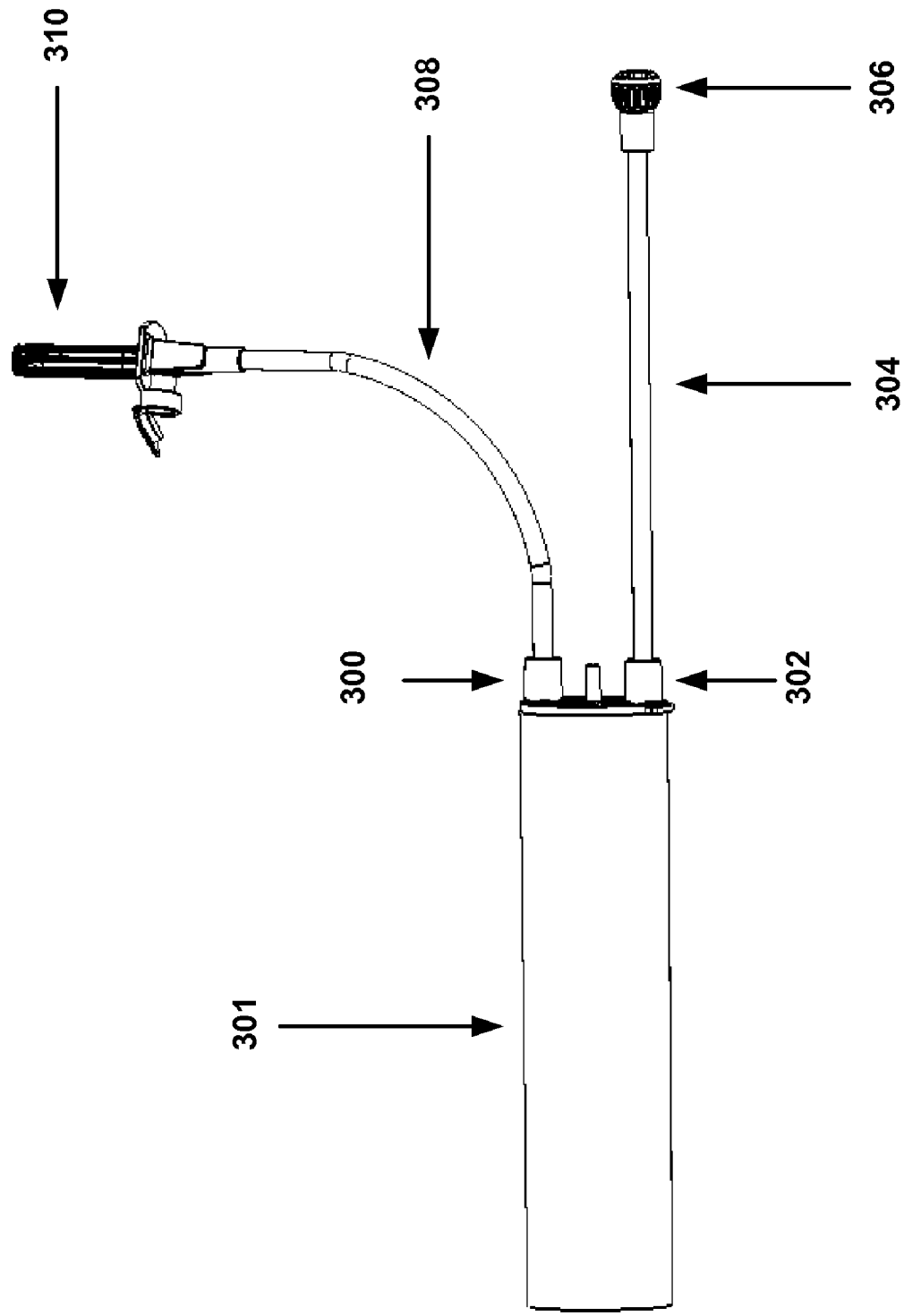
FIG. 3 is a perspective diagram of an example syringe that may be used with a powered medical fluid injection device, according to one embodiment.

Device 100 includes a control panel 102, an injector head 104, a sleeve 108 to hold a pressurizing unit, a reservoir holder 110, a module 112, a patient manifold sensor 114, and an air detector 116. Injector head 104 includes a pump 106 and also includes one or more processors used to control and/or monitor injector head 104, control panel 102, the pressurizing unit within sleeve 108, patient manifold sensor 114, and air detector 116 of device 100. Reservoir holder 110 is capable of holding a fluid reservoir that contains an amount of fluid to be drawn into the syringe during operation of device 100. For example, reservoir holder 110 may hold a reservoir of contrast media or diluent. A second reservoir holder (not shown) may hold a diluent (e.g., saline) for use in pump 106. FIG. 3 shows an example of a syringe that may be used within sleeve 108, according to one embodiment. Patient manifold sensor 114 may, in some cases, be connected to a patient manifold, as will be described in reference to FIG. 1B.

An operator of device 100, such as a clinician, may use control panel 102 to set up various parameters and/or protocols to be used for a given injection procedure. For example, the operator may interact with control panel 102 to enter injection parameters for flow rate, maximum injection volume, maximum injection pressure, rise time, or other parameters. In one embodiment, control panel 102 includes a touch-screen panel.

Pump 106 is capable of pumping fluid. In one embodiment, pump 106 is a peristaltic pump. In this embodiment, tubing and a fluid reservoir (not shown) are coupled to and through pump 106. Pump 106 pumps fluid from the fluid reservoir through the tubing towards module 112. In the example of FIG. 1A, both pump 106 and the syringe contained within sleeve 108 are capable of delivering fluid from device 100 into a catheter. Pump 106 is driven by a motor that is part of pump 106, and the plunger within the syringe is driven by a motor assembly, including an actuator, that is part of injector head 104. In one embodiment, injector head 104 includes a processor that drives the motor assembly.

In one embodiment, reservoir holder 110 holds a fluid reservoir that is coupled to input fluid tubing. This input fluid tubing is coupled to the syringe, such that when the plunger within the syringe is moved in a first direction by the motor, fluid is drawn from the reservoir into the syringe. The syringe within sleeve 108 is further coupled to output tubing. When the plunger within the syringe is moved in a second, opposite direction, fluid is expelled out of the syringe into the output tubing. In one embodiment, the syringe is a dual-port syringe, such that the input tubing is coupled to one port of the syringe, and the output tubing is coupled to another port of the syringe. FIG. 3 shows an example of such a dual-port syringe, which will be described in more detail below.

Patient manifold sensor 114 is coupled to a manifold valve (not shown), according to one embodiment. This manifold valve controls flow of fluid from tubing coupled to either the syringe in sleeve 108 or pump 106. In one embodiment, the manifold valve is coupled to output tubing from the syringe and also to tubing that runs through pump 106. Tubing also is coupled between the manifold valve and air detector 116. After passing through air detector 116, the tubing is then coupled to a patient line or catheter (not shown), such that fluid can ultimately be delivered from device 100 to a patient.

The manifold valve held by the patient manifold sensor 114 is capable of controlling the flow of fluid from the syringe and pump 106 to an external catheter. In one embodiment, the manifold valve has a first position that allows only fluid from the syringe to be delivered to the catheter. The manifold valve has a second position that allows only fluid from pump 106 to be delivered to the catheter. In one embodiment, the manifold valve may comprise a spring-biased spool valve, but in other embodiments, other types of valves, including check valves, may also be used. Patient manifold sensor 114 can detect the manifold valve position and report this position to injector head 104 for safety purposes.

Device 100 also includes air detector 116. Tubing that runs from device 100 to an external catheter passes through air detector 116, which is capable of detecting air bubbles or air columns within the tubing. If air detector 116 detects a measureable or otherwise significant amount of air within the tubing, it is capable of generating an alarm signal for injector head 104. In such a case, a warning or alarm message may be displayed to the operator on control panel 102, indicating that air has been detected. In addition, in one embodiment, device 100 may automatically pause, or terminate, a fluid injection procedure if air detector 116 has detected air in the tubing, such that the air is not delivered to the catheter.

Because device 100 may be used for many injections and patient procedures, injection fluids may need to be continuously replaced. For example, when the reservoir held by holder 110 becomes empty, it may need to be manually replaced with a new (full) reservoir by the operator. In addition, the syringe in sleeve 108 may need to be supplied with injection fluid from time to time, such that there is sufficient fluid within the syringe to perform injections for patient procedures.

Figure 1B:
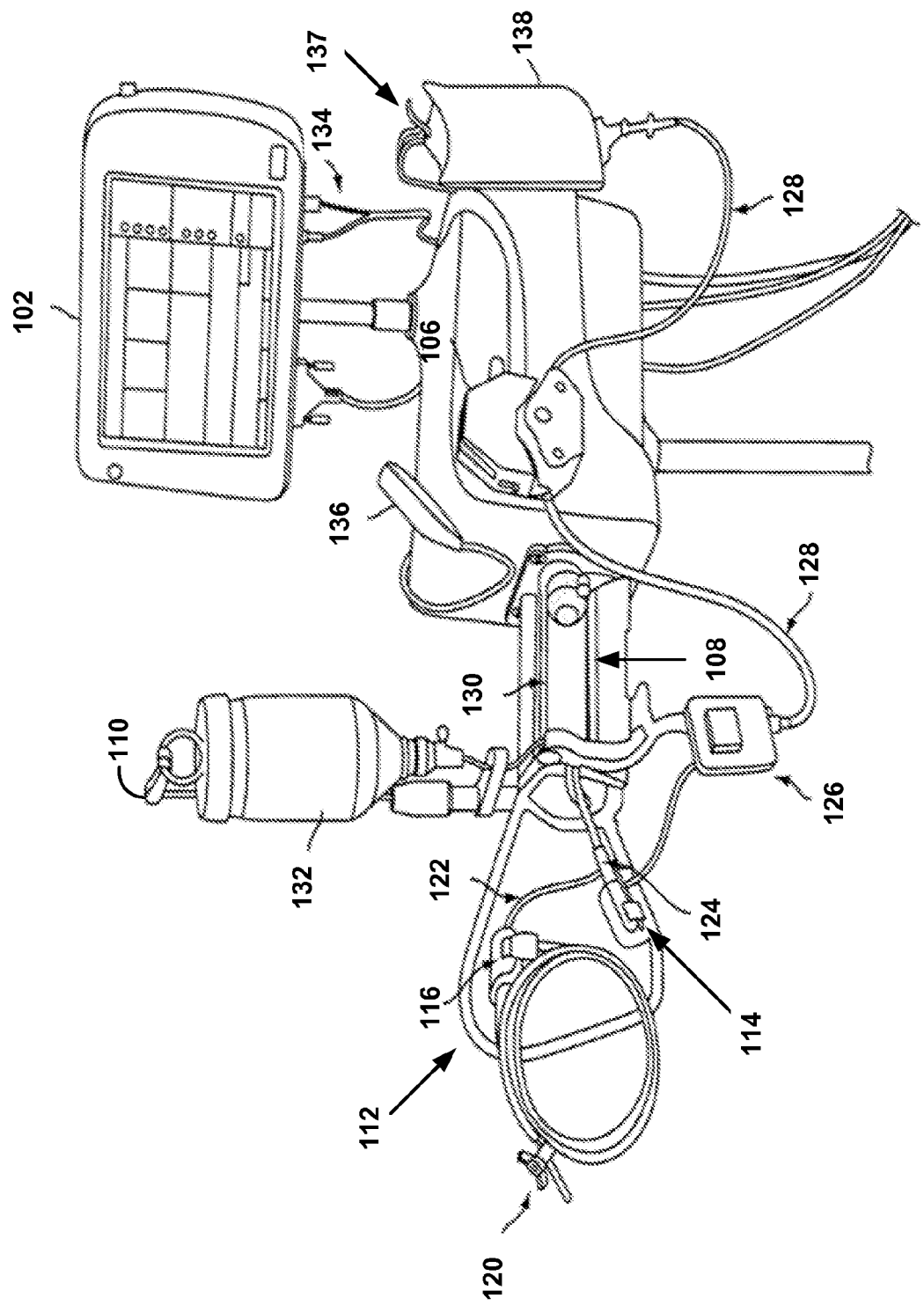
FIG. 1B is a perspective diagram of one embodiment of the powered medical fluid injection device of FIG. 1A connected to various components, including fluid reservoirs and tubing.

FIG. 1B is a perspective diagram of one embodiment of the powered medical fluid injection device 100 of FIG. 1A connected to various components, including fluid reservoirs and tubing. For example, FIG. 1B shows a first fluid reservoir 132 and a second fluid reservoir 138. First fluid reservoir 132 contains a first fluid, such as contrast media. An operator may hang first fluid reservoir 132 on reservoir holder 110. In some cases, first fluid reservoir 132 may be a glass reservoir, while in other cases, it may be a plastic reservoir. The fluid contained within first fluid reservoir 132 may be drawn through tubing and into a pressurizing unit 130 (e.g., a syringe) that has been inserted into sleeve 108 during operation. During an automatic replenishment operation, device 100 may automatically supply pressurizing unit 130 with an amount of fluid from first fluid reservoir 132.

Second fluid reservoir 138 may contain a second fluid, such as saline. An operator may hang second fluid reservoir 138 on a hook 137. In some cases, second fluid reservoir 138 may be a plastic reservoir, such as a bag. The fluid contained within second fluid reservoir 138 may be drawn through tubing 128 through operation of pump 106.

FIG. 1B also shows that a hand-control device 136 is coupled to control panel 102 via a connector 134. In one embodiment, hand-control device 136 may be connected to another component of device 100 other than control panel 102. As shown in FIG. 1B, hand-control device 136 is coupled to tubing, cabling, or wiring, which connects hand-control device 136 to connector 134. Connector 134 may then be connected to or disconnected from control panel 102. An operator may manipulate hand-control device 136 to control injection of fluid from device 100. For example, the operator may use hand-control device 136 as a variable-rate control device to variably control the rate of flow of fluid from device 100 (e.g., flow of fluid out of pressurizing unit 130). In one embodiment, hand-control device 136 may comprise an electrical device. In one embodiment, hand-control device 136 may comprise a pneumatic device.

Tubing 128 is coupled to a pressure transducer 126. Pressure transducer 126 is also coupled to output, high-pressure tubing 122, which may be connected to a patient line via connector 120. When high-pressure tubing 122 is connected to a patient line (within a patient), pressure transducer 126 is capable of functioning as a hemodynamic monitor for the patient. Pressure transducer 126 converts detected pressures into electrical signals that may be monitored or otherwise used by device 100 or another monitoring device. High-pressure tubing 122 also runs through air detector 116. Air detector 116 is capable of detecting the presence of air (e.g., air bubbles or columns) within fluid that may be flowing through high-pressure tubing 122.

FIG. 1B also shows a manifold valve 124. This manifold valve 124 is connected to high-pressure tubing 122, as well as patient manifold sensor 114. Manifold valve 124 is capable of controlling a flow of fluid from pressurizing unit 130 and/or through pump 106 to high-pressure tubing 122. For example, in one embodiment, when manifold valve 124 is in a first position, fluid may flow from pressurizing unit 130 to high-pressure tubing 122. When manifold valve 124, however, is in a second position, fluid may flow through pump 106, via tubing 128, to high-pressure tubing 122. In one embodiment, manifold valve 124 may allow fluid flow to high-pressure tubing 122 from only one of pressurizing unit 130 or pump 106 at a time.

Figure 2A:
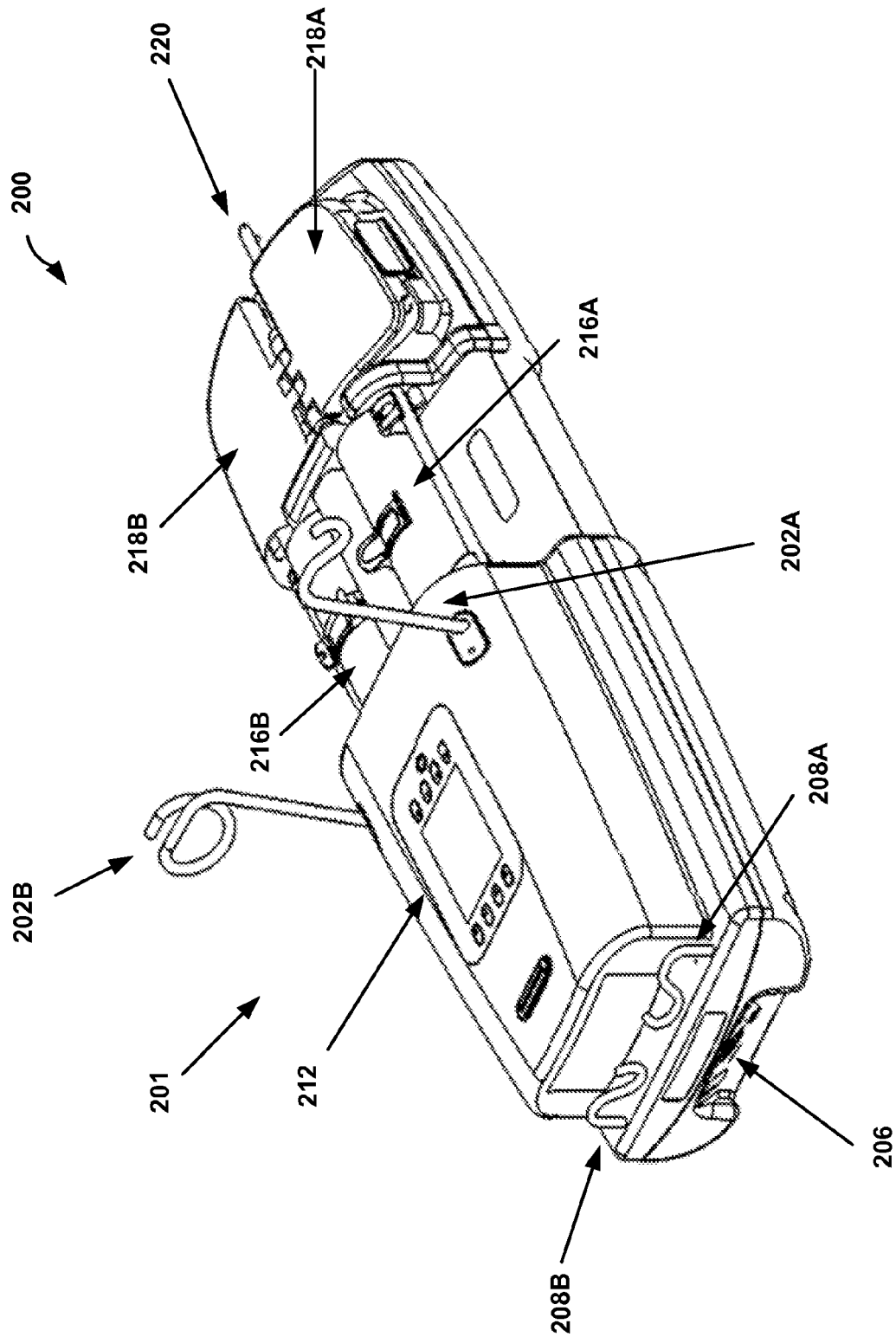
FIGS. 2A-2E are various perspective diagrams of another embodiment of a powered medical fluid injection device, or device components, that may be connected to a fluid connection assembly.

FIG. 2A is a perspective diagram of another embodiment of a powered injection device 200 that may be used to perform various functions and, when operable, may be connected to a fluid connection assembly. In FIG. 2A, device 200 includes a first primary reservoir holder 202A, a second primary reservoir holder 202B, an electrical connection interface 206, a first backup reservoir holder 208A, a second backup reservoir holder 208B, a control panel 212, a first syringe sleeve 216A, a second syringe sleeve 216B, a first front-end assembly 218A, a second front-end assembly 218B, and a patient connection guide rod 220. In the embodiment of FIG. 2A, the pressurizing units that are used to deliver medical fluid are syringes that are contained within sleeves 216A and 216B. Injector head 201 includes reservoir holder 202A, reservoir holder 202B, connection interface 206, reservoir holder 208A, reservoir holder 208B, and control panel 212. Injector head 201 further includes one or more processors used to control and/or monitor the components of injector head 201 and other components of device 200.

Reservoir holder 202A is capable of holding a first reservoir of medical fluid, while reservoir holder 202B is capable of holding a second reservoir of medical fluid. In one embodiment, reservoir holder 202A holds a reservoir of a first type of fluid, such as contrast media, while reservoir holder 202B holds a reservoir of a second, different type of fluid, such as a diluent (e.g., saline). Different forms of reservoirs (e.g., bottles, bags) may be used with reservoir holders 202A and 202B. Because device 200 may be used to inject medical fluid over multiple patient procedures, the reservoirs held by holders 202A and 202B may need to be replaced over time. Typically, an operator of device 200 manually replaces the reservoirs on holders 202A and 202B. For operator convenience, device 200 additionally includes backup holders 208A and 208B. The operator may store backup fluid reservoirs on holders 208A and 208B. When a reservoir on primary holder 202A or 202B runs empty and needs to be replaced, operator may quickly and easily access a new fluid reservoir from one of backup holders 208A or 208B and attach to primary holder 202A or 202B.

Device 200 includes electrical connection interface 206 to directly or indirectly couple device 200 to an external medical device, such as a medical imaging device. Typically, device 200, when used as a contrast media injection device, works in conjunction with a medical imaging device. For example, device 200 may work in conjunction with a medical imaging device during an angiographic or CT procedure. Connection interface 206 is used to directly or indirectly connect device 200 to such an imaging device. In one embodiment, device 200 may transmit injection and/or control information to an external imaging device via interface 206, and may receive imaging and/or control information from the external imaging device via interface 206, as well.

FIG. 2A shows that device 200 also includes control panel 212. Control panel 212 is located on the top side of example device 200. The operator may interact with control panel 212 to program various injection procedure parameters and/or protocols that may be used for injection procedures. The operator may also use control panel to set up device 200 for use, to begin, pause, resume, or end a procedure, or to view various injection-related information (such as flow rate, volume, pressure, rise time, procedure type, fluid information, and/or patient information). FIG. 2A shows various user-activated buttons on the side of control panel 212. However, in one embodiment, control panel 212 may include a touch-activated screen.

In one embodiment, a separate, larger control panel (not shown) may also be in communication with device 200. In this embodiment, the larger control panel provides similar operator functionality to that provided by control panel 212. However, the larger control panel may be mounted to a rail of a bed on which a patient is lying, or may be mounted to other devices separate from device 200. In one embodiment, the larger control panel looks similar to control panel 102 shown in FIG. 1A.

Device 200 is a dual-syringe device that includes two syringes contained within sleeves 216A and 216B. Both syringes are capable of delivering medical fluid to a patient.

In one embodiment, the syringe within sleeve 216A is capable of drawing in fluid from a fluid reservoir coupled to holder 202A, and the syringe within sleeve 216B is capable of drawing in fluid from a fluid reservoir coupled to holder 202B. For example, these syringes may draw in fluid during a fluid replenishment operation. Each syringe is coupled to a motor/actuator assembly (not shown) that drives a plunger in one of two directions. During a fluid replenishment cycle, for example, a motor/actuator assembly of device 200 may drive a plunger within the syringe in sleeve 216A in one direction to draw fluid from a reservoir coupled to holder 202A into the syringe. During an injection cycle, the motor/actuator assembly of device 200 may drive the plunger within this syringe in the opposite direction to expel fluid. In one embodiment, device 200 contains two distinct motor/actuator assemblies, such that one assembly drives the syringe within sleeve 216A while another drives the syringe within sleeve 216B. These motor/actuator assemblies are part of injector head 201, and may individually be controlled or monitored by the one or more processors included within injector head 201.

Fluid input tubing couples the syringes within sleeves 216A and 216B to the fluid reservoirs and to output lines, according to one embodiment. In one embodiment, the syringes each are dual-port syringes (such as the dual-port syringe shown in FIG. 3). In this embodiment, one syringe port is used for input tubing that is coupled to a fluid reservoir, while the second port is used for output tubing that is operatively coupled to an output (patient) line through assemblies 218A or 218B.

Front-end assembly 218A is associated with sleeve 216A, and front-end assembly 218B is associated with sleeve 216B. Output tubing from the syringe in sleeve 216A runs through assembly 218A and out to a patient line, while output tubing from the syringe in sleeve 216B runs through assembly 218B and out to the patient line. Each assembly 218A and 218B includes a door, or cover, which may be opened and closed by the operator. For the example, the operator may open the door when loading tubing and may be closed upon loading. In one embodiment, each door may be made of a transparent or translucent material, such that the operator may see inside the contents of the assembly 218A or 218B even when the door is closed.

In one embodiment, each front-end assembly 218A and 218B includes air detectors and valve components (not shown). Air detectors are used to detect air bubbles or air columns within the fluid tubing that is used. The valve components are used to allow or restrict fluid flow through tubing. For example, when pinch valves are used, the valves pinch fluid tubing to restrict fluid flow in one state, but stay open to allow fluid flow in another state. Various different forms of valves may be used within assemblies 218A and 218B. In addition, various different forms of air detectors (e.g., ultrasonic, optical) may be used, as well.

In one embodiment, the input and output tubing that is coupled to the syringe in sleeve 216A runs through front-end assembly 218A, and the input and output tubing that is coupled to the syringe in sleeve 216B runs through front-end assembly 218B. In this embodiment, each assembly 218A and 218B contains a first pinch valve and a first air detector coupled to the input tubing for the respective syringe, and further contains a second pinch valve and a second air detector coupled to the output tubing for the respective syringe. These components are more clearly shown in FIG. 2D and will be discussed in more detail below.

Figure 4:
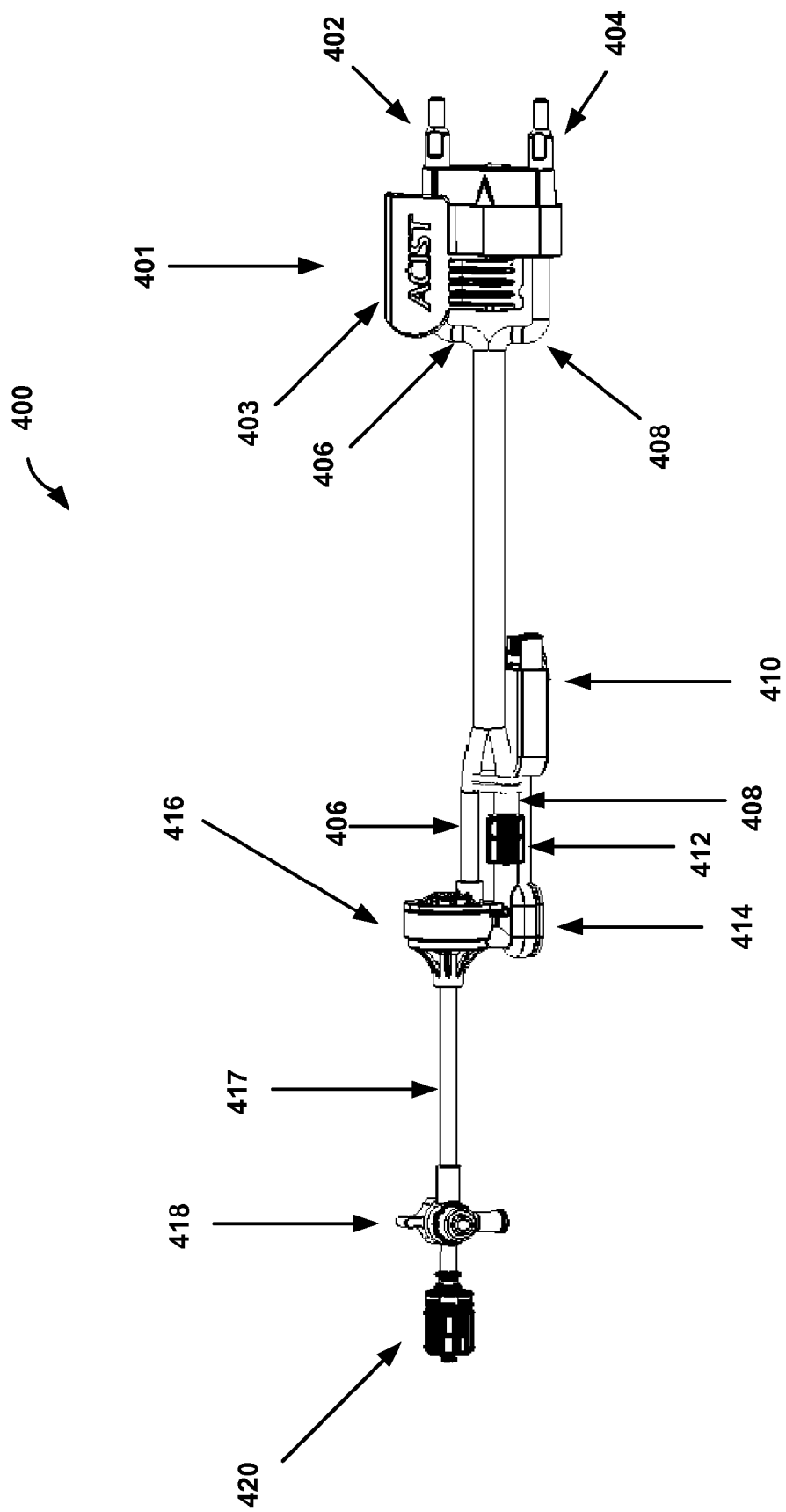
FIG. 4 is a perspective diagram of a patient line that may be used with a powered medical fluid injection device, according to one embodiment.

FIG. 2A also shows a patient connection guide rod 220. The output tubing from syringes 216A and 216B run through front-end assemblies 218A and 218B, respectively, and are then coupled to a patient line, or kit (not shown). The patient line is a single-use line, according to one embodiment, that is used for a single patient procedure. Each patient line may be connected to and disconnected from the output tubing running through front-end assemblies 218A and 218B. The patient line is connected to the output tubing via connection guide rod 220, according to one embodiment. The patient line may slide over connection guide rod 220 in order to become coupled with the output tubing. In one embodiment, the patient line includes two tubing elements, each element corresponding to one of the output tubing elements of the syringe in sleeve 216A or 216B. An example patient line is shown in FIG. 4 and will be discussed in more detail below.

In one embodiment, a medical fluid injection device, such as device 200, may include a plurality of pressurizing units, including three or more pressurizing units. Each of these pressurizing units may be included within a separate sleeve during operation. In some cases, multiple pressurizing units may contain the same type of fluid. For example, a first pressurizing unit may contain contrast media, a second pressurizing unit may contain a diluent (e.g., saline), and a third pressurizing unit may contain contrast media. In this scenario, the third pressurizing unit may comprise a backup, or secondary, source of contrast media. In this example, the first and third pressurizing units may both be coupled to a common front-end assembly, such as a front-end assembly similar to 218A or 218B.

Figure 2B:
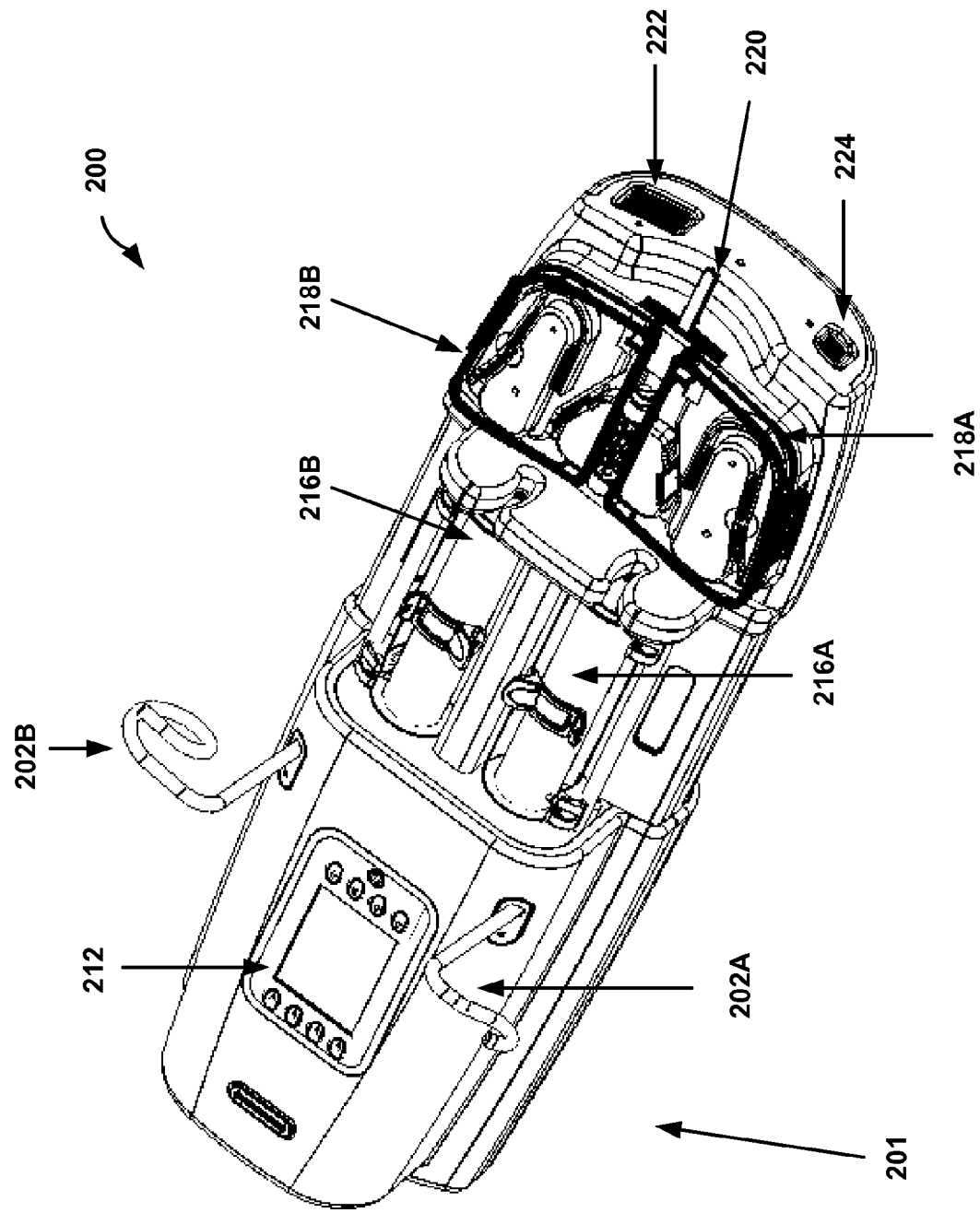

FIG. 2B is another perspective diagram of device 200 shown in FIG. 2A. In FIG. 2B, sleeves 216A and 216B, along with front-end assemblies 218A and 218B, can be more clearly seen. Although the doors of assemblies 218A and 218B are closed in the example of FIG. 2B, they are made of a semi-transparent material, such that the interior pinch valve and air detector components may be more clearly seen. FIG. 2B also shows connection ports 222 and 224. In one embodiment, a pressure transducer connector (such as one coupled to connector 410 shown in FIG. 4), may be connected to connection port 224. The pressure transducer connector is operatively coupled to a pressure transducer, which measures patient hemodynamic signals on the patient line. By connecting a pressure transducer to connection port 224, device 200 is capable of utilizing and processing hemodynamic pressure signals of a patient that are detected in the patient line.

Device 200 also includes connection port 222, which may be connected to a hand-control device (not shown). In one embodiment, the hand-control device is a disposable component that may be used by the operator for a single patient procedure. The hand-control device may control the operation of one or both of syringes in sleeves 216A and 216B. For example, the operator may push a button or otherwise interact with the hand-control device to cause a motor/actuator assembly to inject fluid from the syringe in sleeve 216A, and may push another button or otherwise interact with the hand-control device to cause a motor/actuator assembly to inject fluid from the syringe in sleeve 216B. Thus, if the syringe in sleeve 216A contains contrast media, and the syringe in sleeve 216B contains a diluent, the operator may push one button on the hand-control device to inject contrast into the patient line, and may push another button to inject saline. In one embodiment, the hand-control device contains variable-rate functionality, such that the harder the operator pushes on a button or actuates a component, the greater the flow rate of injected fluid from the syringe in sleeve 216A or 216B.

Figure 2C:
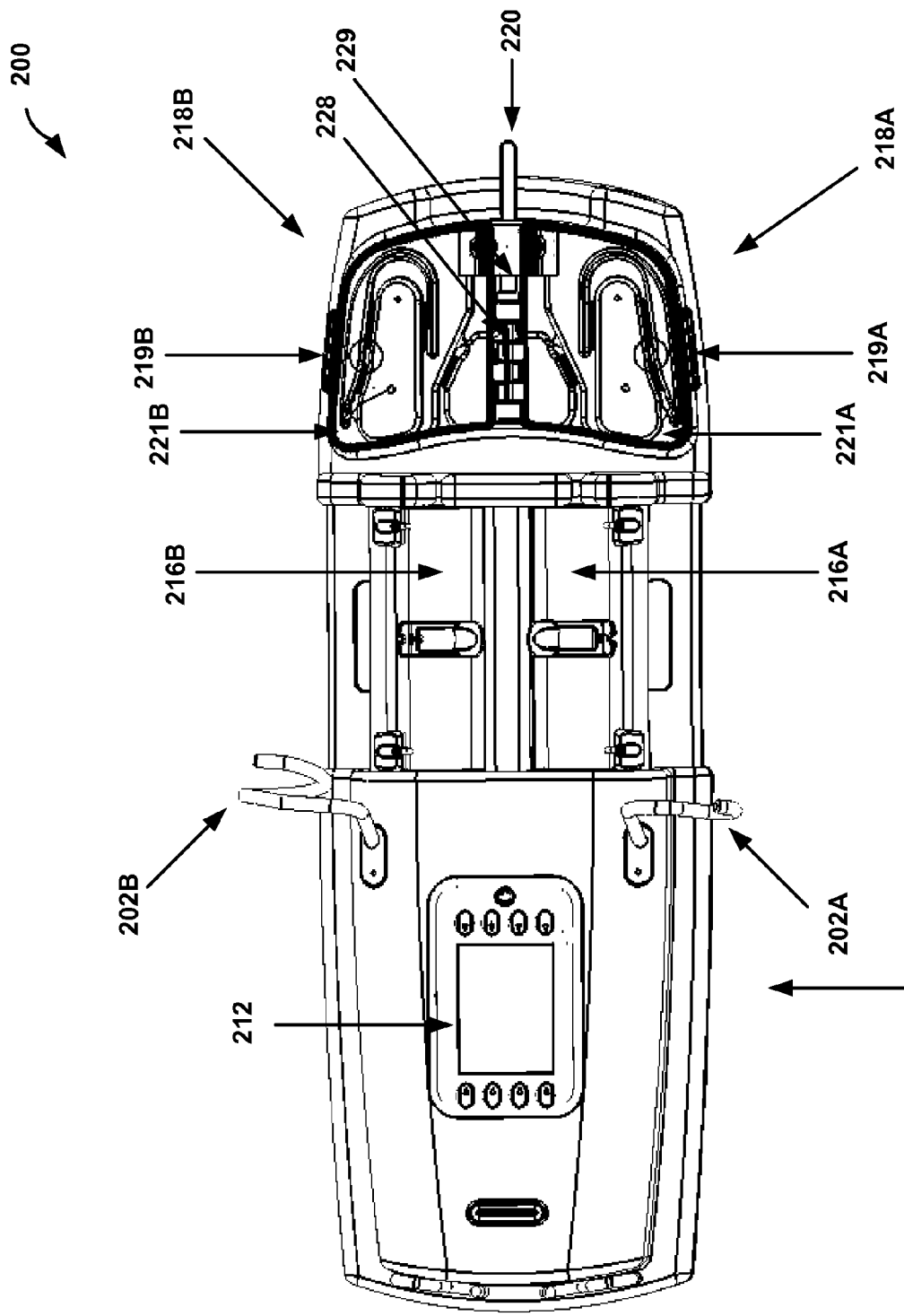

FIG. 2C is another perspective diagram of device 200. FIG. 2C shows a top view of device 200, according to one embodiment.

FIG. 2C also shows doors 221A and 221B on front-end assemblies 218A and 218B, respectively. As noted above, in one embodiment, each of assemblies 218A and 218B include a moveable door 221A and 221B, respectively. Door 221A covers assembly 218A, and door 221B covers assembly 218B. In the embodiment of FIG. 2C, doors 221A and 221B are made of a transparent, or semi-transparent, material, such that an operator may see the contents of assemblies 218A and 218B (which are shown in more detail in FIG. 2D). Door 221A includes a handle 219A, and door 221B includes a handle 219B. The operator may utilize handles 219A and 219B to open and close doors 221A and 221B, respectively. Doors 221A and 221B are coupled to one or more hinges 228, which allow doors 221A and 221B to be opened and closed.

Also shown in FIG. 2C is a pivot pin 229. Pivot pin 229 is inserted through hinges 228, according to one embodiment, to securely allow doors 221A and 221B to be freely opened and closed by an operator. Doors 221A and 221B pivot about an axis that runs through pivot pin 229.

In one embodiment, pivot pin 229 is screwed into place. Pivot pin 229 may also be removed by an operator. For example, the operator may unscrew pivot pin 229 and remove it from front-end assemblies 218A and 218B. After pivot pin 229 has been removed, doors 221A and 221B may also be removed from assemblies 218A and 218B. For example, the operator may choose to remove doors 221A and 221B if the operator wishes to clean or replace doors 221A and 221B.

Figure 2D:
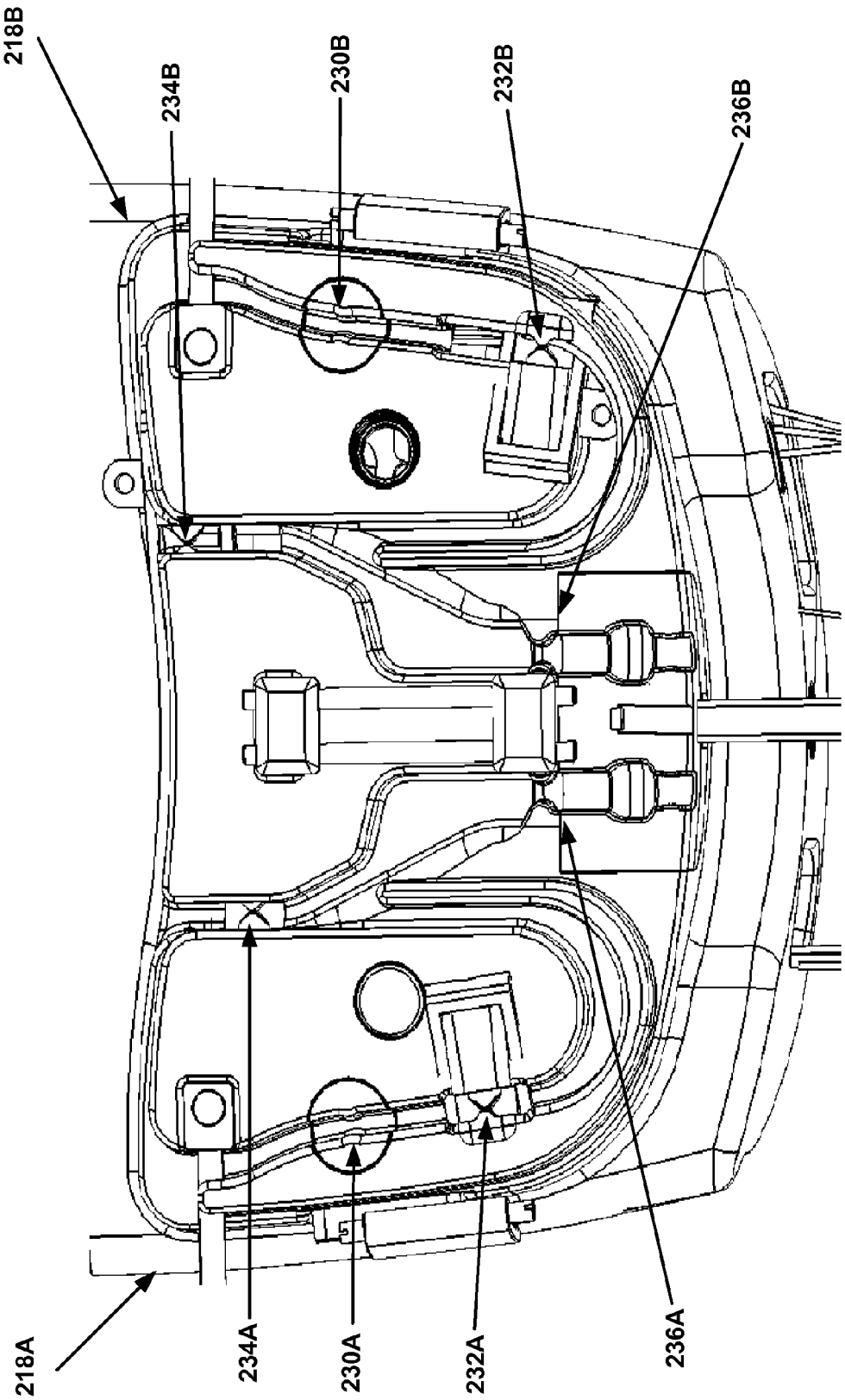

FIG. 2D is a perspective view of front-end assemblies 218A and 218B shown in more detail, according to one embodiment. Although doors 221A and 221B are not shown in FIG. 2D, they are made of a transparent, or semi-transparent, material, such that the contents of assemblies 218A and 218B may be more clearly seen by an operator, even when doors 221A and 221B are closed.

Front-end assembly 218A includes a first air detector 230A, a first pinch valve 232A, a second pinch valve 234A, and a second air detector 236A. Input tubing from a reservoir on holder 202A runs through air detector 230A and pinch valve 232A and into a syringe in sleeve 216A via a first syringe port, according to one embodiment. Output tubing coupled to a second syringe port of the syringe in sleeve 216A runs through pinch valve 234A and air detector 236A and is then coupled an external patient line, or kit (such as the one shown in FIG. 4). Air detector 230A is used to detect air bubbles or columns within the input tubing, and air detector 236A is used to detect air bubbles or columns within the output tubing. Air detectors 230A and 236A may comprise acoustic-based, optical-based, or other forms of air detectors. If either or both of air detectors 230A and 236A detect a measurable amount of air in the input and/or output tubing, these detectors may propagate signals to injector head 201 of device 200. One or more processors of injector head 201 may process these received signals. Injector head 201 may provide a warning message or alert to the operator via control panel 212, such that the operator may take appropriate action. Injector head 201 may also, in one embodiment, automatically pause or terminate any injection of fluid from the syringe in sleeve 216A if air has been detected in the input and/or output tubing, by controlling operation of the motor/actuator assembly driving the syringe.

Pinch valve 232A controls a flow of fluid from input tubing into the syringe in sleeve 216A. Injector head 201 controls the operation of pinch valve 232A. When injector head 201 opens pinch valve 232A, fluid may flow from the reservoir connected to holder 202A and into the syringe. When pinch valve 232A is closed, no fluid flow is permitted within the input tubing. For example, when injector head 201 is supplying the syringe with fluid, it may open pinch valve 232A to allow fluid flow in the input tubing, but it may also close pinch valve 234A, to prohibit any fluid flow in the output tubing. The plunger within the syringe may be moved in a first direction (by the motor/actuator assembly) to supply fluid to the syringe. When a fluid injection occurs, the motor/actuator assembly will move the plunger within the syringe in a second, opposite direction. Injector head 201 may close pinch valve 232A during an injection procedure, to prohibit fluid flow in the input tubing. However, injector head 201 may open pinch valve 234A, to allow fluid flow in the output tubing during such a procedure. In such fashion, injector head 201 utilizes pinch valves 232A and 234A to control fluid flow in the input and output tubing during various operations (e.g., replenishment and injection operations).

In one embodiment, pinch valves 232A and 234A are solenoid-based pinch valves. In other embodiments, other forms of pinch valves 232A and 234A may be used, such as pneumatic-based valves. In one embodiment, pinch valves 232A and 234A have default states in the closed position. Thus, when device 200 is neither supplying fluid into nor injecting fluid from the syringe in sleeve 216A, both pinch valves 232A and 234A are closed. Pinch valves 232A and 234A may then be opened by device 200 when energy is actively applied to pinch valves 232A and/or 234A. When no energy is applied to pinch valves 232A and/or 234A, they return to a default, closed position. Thus, if there are any power failures to device 200, valves 232A and 234A will return to closed position. This may help improve the safety of device 200.

Similarly, front-end assembly 218B includes a first air detector 230B, a first pinch valve 232B, a second pinch valve 234B, and a second air detector 236B. Input tubing from a reservoir connected to holder 202B runs through air detector 230B and pinch valve 232B and into a first syringe port of the syringe in sleeve 216B. Output tubing coupled to a second syringe port of the syringe runs through pinch valve 234B and air detector 236B, and may then be coupled to a patient line. The components within device 218B function similarly to those contained within device 218A as described above, according to one embodiment.

Figure 2E:
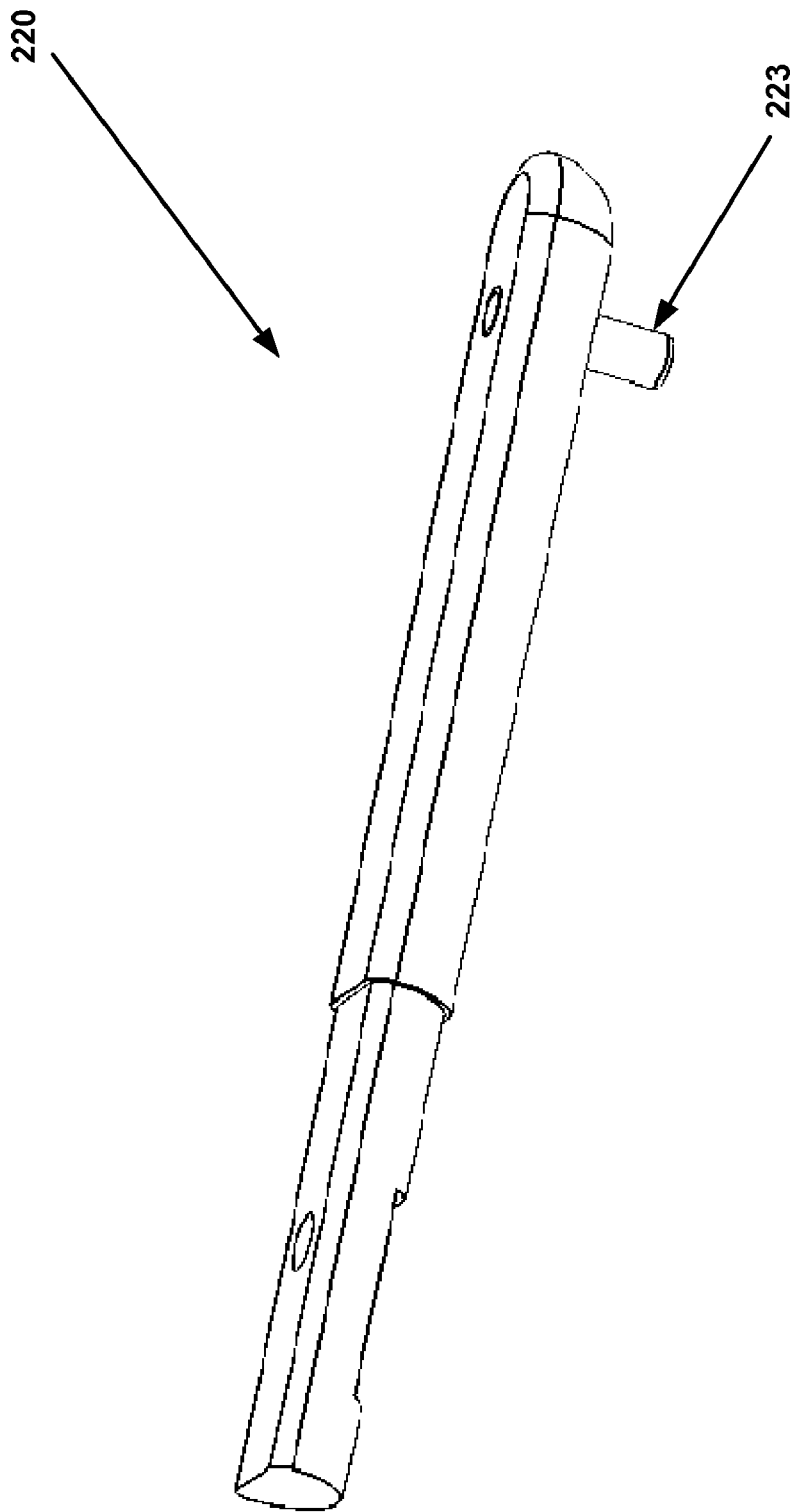

FIG. 2E is a perspective diagram of guide rod 220 of device 200 in more detail, according to one example embodiment. In this example embodiment, guide rod 220 includes a pin 223. Pin 223 comprises a portion of guide rod 220 that may mate or otherwise connect with external components, such as a fluid connection assembly of a patient line, as will be described in further detail below. In one embodiment, the fluid connection assembly may include at least one fluid connector, a mating mechanism, and a locking mechanism. The mating mechanism is coupled to the at least one fluid connector and configured to connect the at least one fluid connector to high-pressure tubing of device 200. The locking mechanism is coupled to the mating mechanism and is movable into a locked position or an unlocked position. When in the locked position, the fluid connection assembly becomes affirmatively coupled to device 200. For example, the locking mechanism may engage or receive pin 223 of guide rod 220 when it is in the locked position, as will be described in more detail below, such that the locking mechanism becomes affirmatively coupled to guide rod 220. For example, pin 223 may be inside or otherwise locked within a groove of a portion of the fluid connection assembly when the locking mechanism is in the locked position. When moved to the unlocked position, the locking mechanism may disengage pin 223 of guide rod 220, such that the locking mechanism becomes removably decoupled from guide rod 220 of device 200. These aspects will be described in further detail below in reference to FIGS. 5A-5D.

FIG. 3 is a perspective diagram of an example syringe 301 that may be used within device 200, according to one embodiment. Syringe 301 may be loaded in either sleeve 216A or 216B. If syringe 301 is loaded into sleeve 216A, it may be coupled to a fluid reservoir connected to holder 202A (FIG. 2A), and may further be coupled to a patient line (FIG. 4).

Syringe 301 is a dual-port syringe in the example of FIG. 3. Input port 300 is coupled to input tubing 308, and output port 302 is coupled to output tubing 304. Input tubing is coupled to a connector 310, which may be connected to a fluid reservoir in holder 202A, assuming syringe 301 is loaded into sleeve 216A. For example, if connector 310 is a spike, the spike may be inserted into a bottle of medical fluid connected to holder 202A. Output tubing 304 is coupled to a connector 306, which couples output tubing 304 to a separate patient line. In one embodiment, connector 306 is a Luer-type connector.

Fluid is drawn from the fluid reservoir into port 300 of syringe 301 via input tubing 308. Fluid is expelled from port 302 of syringe 301 into output tubing 304. Input tubing 308 may run through air detector 230A and pinch valve 232A (FIG. 2D) of front-end assembly 218A, which was described in more detail above, while output tubing 304 may run through pinch valve 234A and air detector 236A. In one embodiment, syringe 301, along with input tubing 308, connector 310, output tubing 304, and connector 306, are disposable, multi-use components. That is, these components may be used within device 200 over multiple uses or patient procedures before they are disconnected from device 200 and disposed of. In another embodiment, these components are disposable, single-use components, meaning that they are disposed of after a single patient procedure.

In one embodiment, syringe 301 may also be used in device 100 (FIG. 1A). When used in device 100, connector 310 would be connected to a fluid reservoir on holder 110, and output tubing 304 would run through patient manifold sensor 114.

FIG. 4 is a perspective diagram of a patient line 400 that may be used with injection device 200 shown in FIGS. 2A-2C, according to one embodiment. Patient line 400 includes an assembly 401, a valve 416, a stopcock 418, and a connector 420. Patient line 400 is used to couple device 200 with a catheter that is used to deliver medical fluid to a patient.

Assembly 401 includes a first fluid connector 402 and a second fluid connector 404. When assembly 401 is coupled to device 200, fluid connector 402 is connected with a connector for output tubing that is coupled to one of the syringes in sleeves 216A or 216B, while fluid connector 404 is connected with a connector for output tubing that is coupled to the other syringe. For example, fluid connector 402 may be connected to connector 306 (FIG. 3), which is coupled to output tubing 304 for the syringe in sleeve 216A. Patient line 400 is a disposable kit, in one embodiment, such that connectors 402 and 404 may be connected to and removed from tubing connectors, such as connector 306, by the operator. In one embodiment, patient line 400 is a single-use disposable kit, such that it is connected to device 200 for one patient use, and then subsequently disconnected and discarded.

Assembly 401 may by coupled to device 200 by sliding it over guide rod 220 of device 200 and locking it into place, according to one embodiment. Lever 403 may be used to lock and unlock assembly 401 when it has been coupled to guide rod 220. Lever 403 may be moved into a first position to lock assembly 401 on guide rod 220, and may be moved into a second position to unlock assembly 401. For example, an operator may pull up on lever 403 to lock assembly 401, such that it may be secured and prepared for use during an injection procedure. After the injection procedure has completed, the operator may push down on lever 403 to unlock assembly 401, such that it may be removed from guide rod 220.

Fluid connector 402 is operatively coupled to tubing 406, and fluid connector 404 is operatively coupled to tubing 408. In one embodiment, fluid connector 402 is coupled to the syringe in sleeve 216A, which contains contrast media, while fluid connector 404 is coupled to the syringe in sleeve 216B, which contains a diluent such as saline. Thus, in this embodiment, contrast media is injected into tubing 406 of patient line 400, while diluent is injected into tubing 408. Tubing 406 and 408 are coupled to valve 416, which, in one embodiment, comprises an elastomeric-type valve that allows fluid flow from only one of tubing 406 and 408 to output tubing 417. In one embodiment, valve 416 comprises a one-way valve that allows fluid flow only in the direction towards output tubing 417. Guide rod 220 may help, in some cases, maintain the sterility of connectors 402 and 404 by aligning these connectors, during insertion, to prevent contact with non-sterile items.

As is shown in FIG. 4, tubing 408 is coupled to check valve 412 and transducer 414. In one embodiment, check valve 412 comprises a bi-directional check valve. Transducer 414 comprises a pressure transducer in one embodiment that is capable of measuring hemodynamic signals of a patient when patient line 400 is coupled a catheter that has been inserted into the patient. Transducer connector 410 may be coupled to device 200, such as by way of port 224 (FIG. 2B). When connected, hemodynamic signals generated by transducer 414 may be processed by a processor within device 200.

Output tubing 417 is coupled to stopcock 418 and to connector 420 shown in FIG. 4. Stopcock 418 may be manually manipulated by the operator to control fluid flow, and may also be connected to other external devices, such as a syringe. Connector 420 is used to connect patient line 400 to an external catheter that may deliver fluid to a patient. In one embodiment, connector 420 comprises a Luer-type connector.

In one embodiment, patient line 400 may also be used with device 100 shown in FIG. 1A. When used with device 100, transducer connector 410 is coupled to a mating port within device 100 (not shown), such that a processor of device 100 may process the hemodynamic signals. Assembly 401 may also be coupled in device 100 in this embodiment. Patient line 400 may be coupled to a manifold valve that is coupled to patient manifold sensor 114, such that connection port 402 may be coupled to tubing from the syringe, while connection port 404 may be coupled to tubing running through pump 106. In this embodiment, tubing 417 may also be coupled to, or run through, air detector 116 of device 100.

FIGS. 5A-5D are perspective diagrams of a fluid connection assembly 401 that may be connected to a powered medical fluid injection device, such as device 100 or device 200, according to one embodiment. For purposes of illustration only in the description below, it will be assumed that fluid connection assembly 401 is configured to be connected to device 200.

Fluid connection assembly 401 may include at least one fluid connector, a mating mechanism, and a locking mechanism. In the examples of FIGS. 5A-5D, fluid connection assembly 401 includes two fluid connectors 402 and 404. The mating mechanism, which may be coupled to fluid connectors 402 and 404, may include one or more of a first housing member 502, a second housing member 504, and a lever 403. The locking mechanism may include one or more of first housing member 502, second housing member, and lever 403.

In one embodiment, the mating mechanism of fluid connection assembly 401 is configured to connect fluid connectors 402 and 404 to device 200. The locking mechanism may be coupled to the mating mechanism and may be movable into a locked position or an unlocked position. When the locking mechanism is in the locked position, fluid connection assembly 401 may become affirmatively coupled to device 200, as will be described in more detail below. When the locking mechanism is in the unlocked position, fluid connection assembly 401 may become removably decoupled from device 200.

As is shown in FIGS. 5A-5D, first fluid connector 402 includes a first end connector 508 and a first tube connector 506. Second fluid connector 404 includes a second end connector 512 and a second tube connector 510. First end connector 508 and second end connector 512 may be connected to corresponding tube connectors for tubing that is included, or otherwise inserted in, device 200. For example, an operator may, as described previously, load pressurizing units into sleeves 216A and 216B of device 200. The operator may then load tubing that is connected to each of the two pressurizing units.

For example, the operator may load first tubing (e.g., tubing 304 shown in FIG. 3), which is connected to an output port of a first pressurizing unit (e.g., output port 302 of syringe 301), through pinch valve 234A and air detector 236A of front-end assembly 218A, and may load second tubing, which is connected to an output port of a second pressurizing unit, through pinch valve 234B and air detector 236B of front-end assembly 218B. Tubing running through front-end assemblies 218A and 218B may be coupled to corresponding tube connectors (e.g., connector 306 shown in FIG. 3) that may mate, or connect, with first and second end connectors 508 and 512 when fluid connection assembly 401 has been connected to device 200. Fluid connectors 402 and 404 may be coupled to tubing 406 and 408, respectively, such that fluid may flow from the tubing running through front-end assemblies 218A and 218B and into tubing 406 and 408 through assembly 401. Tubing 408 may run through housing members 502 and 504 via a tube channel 530 in order to be coupled with fluid connector 404.

In one embodiment, the operator may connect fluid connection assembly 401 to device 200 by inserting it onto guide rod 220 of device 200. FIG. 5D shows a perspective view of fluid connection assembly 401 where second housing member 504 includes a guide rod channel 540, which may comprise part of the mating mechanism of fluid connection assembly 401. An operator may manually mate fluid connection assembly 401 to device 200 by inserting guide rod 220 into guide rod channel 540, which receives guide rod 220. The operator may then move fluid connection assembly 401 along the guide rod 220 to connect it to device 200. The insertion of guide rod 220 within guide rod channel 540 may help align fluid connectors 402 and 404 with corresponding connectors (e.g., connector 306 shown in FIG. 3) of device 200. The positive mating mechanism of assembly 401 may help connect fluid connectors 402 and 404 with the corresponding connectors of device 200. More specifically, the mating mechanism may connect end connectors 508 and 512 with corresponding fluid connectors of device 200.

When guide rod channel 540 receives guide rod 220 of device 200, the locking mechanism of assembly 401 may become affirmatively coupled to guide rod 220 when the locking mechanism is in the locked position. For example, the operator may wish to lock assembly 401 into place with respect to guide rod 220 and device 200, such that assembly 401 may not substantially move during operation of device 200 and injection of fluid through assembly 401.

For example, the operator may move lever 403 of assembly 401 into a locked position to affirmatively couple the locking mechanism to guide rod 220. In one scenario, the operator may rotate lever 403 from a substantially flat position with respect to housing members 502 and 504, as shown in FIGS. 5A-5D, into an upright position with respect to housing members 502 and 504, to move lever 403 from an unlocked to a locked position. In this scenario, the locking mechanism is in the locked position when lever 403 is positioned along a first plane that is substantially normal to a plane defined by at least one of housing members 502 and 504. The locking mechanism is in the unlocked position when lever 403 is positioned along a second plane that is substantially co-planar with the plane defined by at least one of housing members 502 and 504. The locking mechanism may become removably decoupled from guide rod 220 of device 200 when the locking mechanism is in the unlocked position.

Figure 5A:
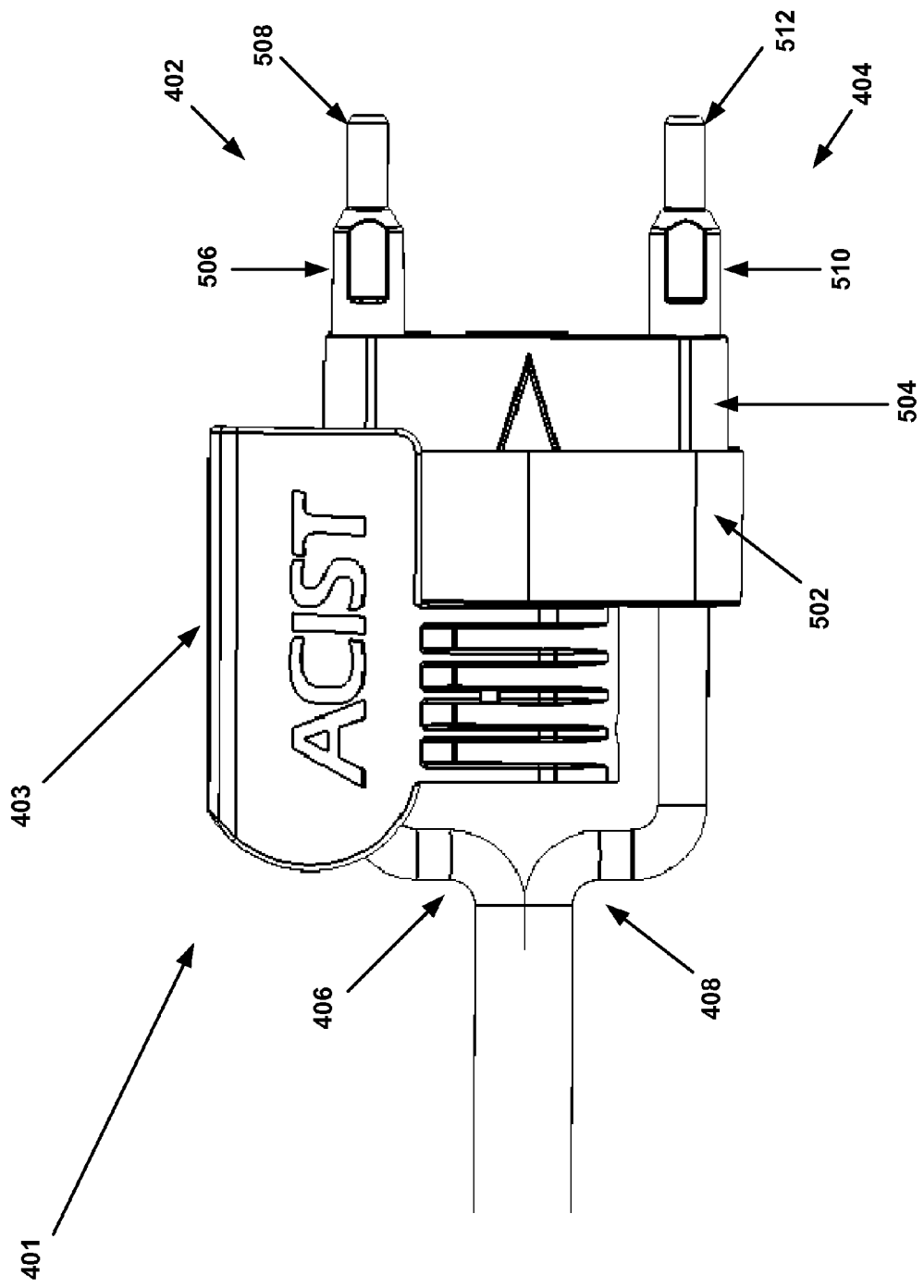
FIGS. 5A-5D are perspective diagrams of a fluid connection assembly that may be connected to a powered medical fluid injection device, according to one embodiment.
Figure 5B:
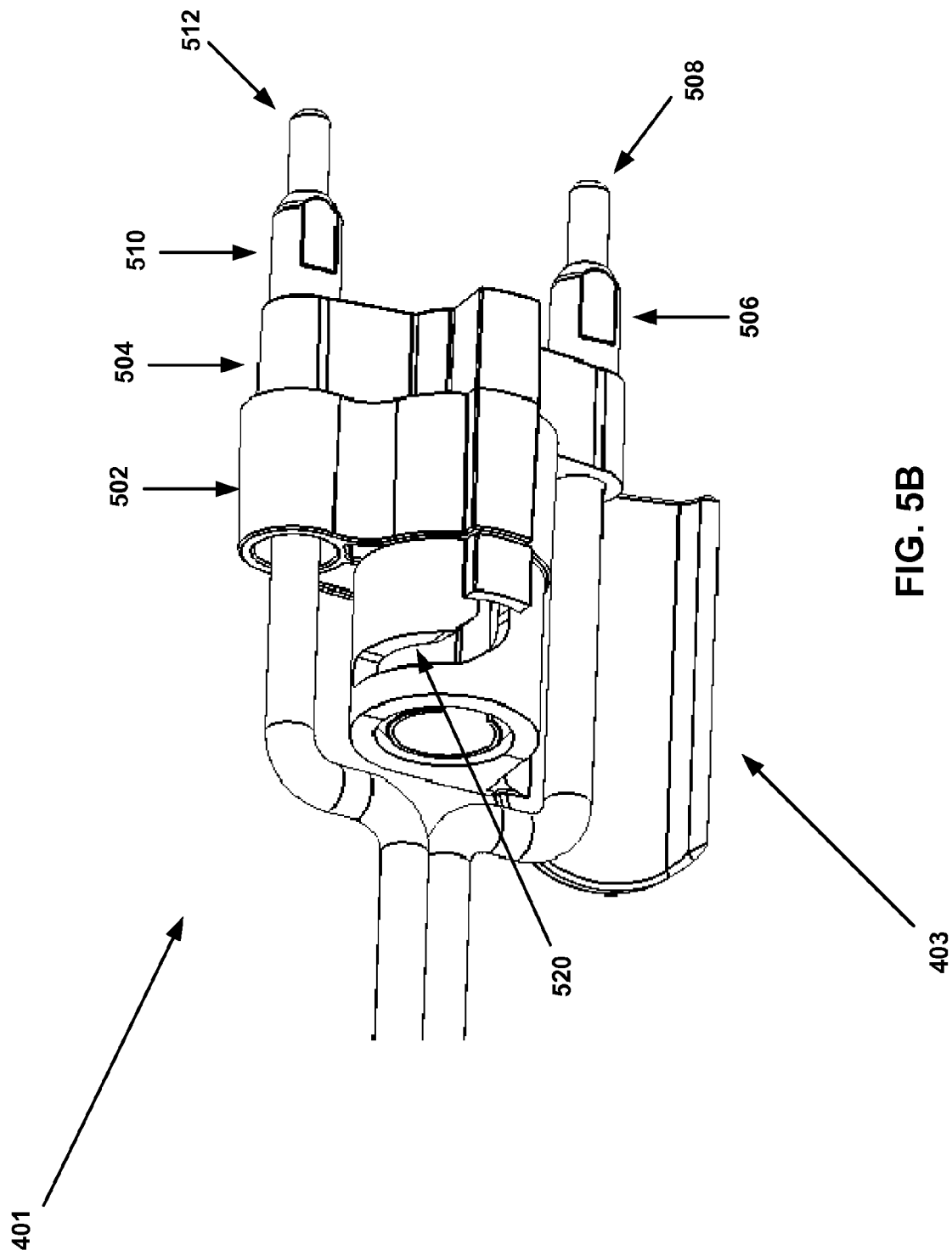
Figure 5C:
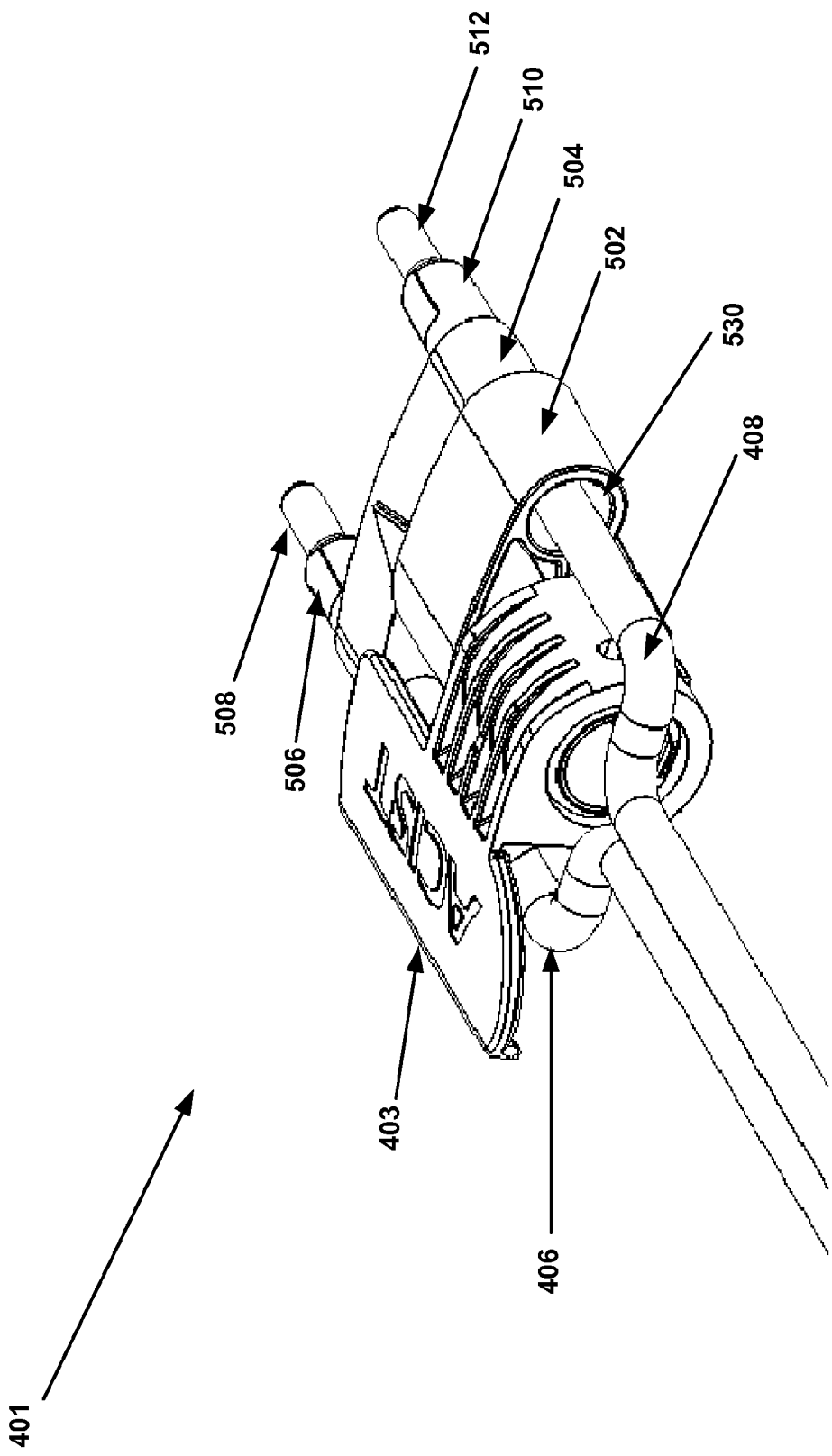
Figure 5D:
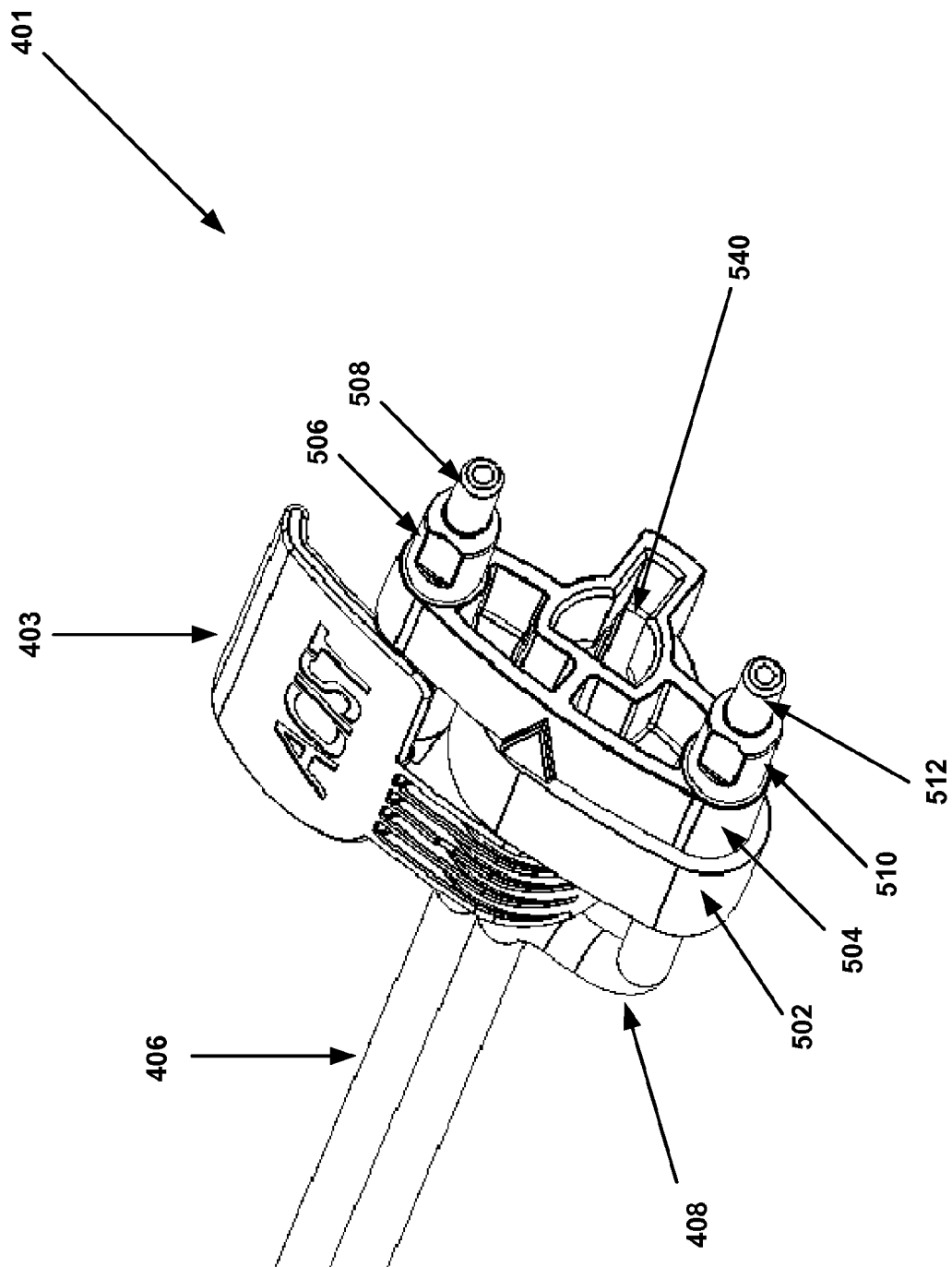

As shown in FIG. 5B, assembly 401 also includes a locking groove 520. This locking groove 520 may be part of the locking mechanism of assembly 401. For example, locking groove 520 may be part of lever 403. In one example, the locking mechanism of assembly 401 is in the locked position when a portion of guide rod 220 is locked within locking groove 520 to restrict movement of assembly 401 on guide rod 220. The locking mechanism is in the unlocked position when the portion of guide rod is 220 unlocked within locking groove 520 to permit movement of assembly 401 on guide rod 220.

For example, the locking mechanism of assembly 401 may be in the locked position when pin 223 (FIG. 2E) of guide rod 220 is locked within locking groove 520 to restrict movement of assembly 401 on guide rod 220. When the locking mechanism has been moved, or rotated, into the locked position, pin 223 of guide rod 220 may slide into, and be firmly engaged within, locking groove 520, such that assembly 401 may not be removed from guide rod 220. In this position, assembly 401 may be considered to be affirmatively coupled to guide rod 220.

The locking mechanism may be in the unlocked position when pin 223 of guide rod 220 is unlocked within locking groove 520 to permit movement of assembly 401 on guide rod 220. When the locking mechanism has been moved, or rotated, into the unlocked position, pin 223 may slide out of, and become disengaged from, locking groove 520, such that assembly 401 may be removed from guide rod 220. When the locking mechanism is in the unlocked position, assembly 401 may be considered to be removably decoupled from guide rod 220.

Figure 7A:
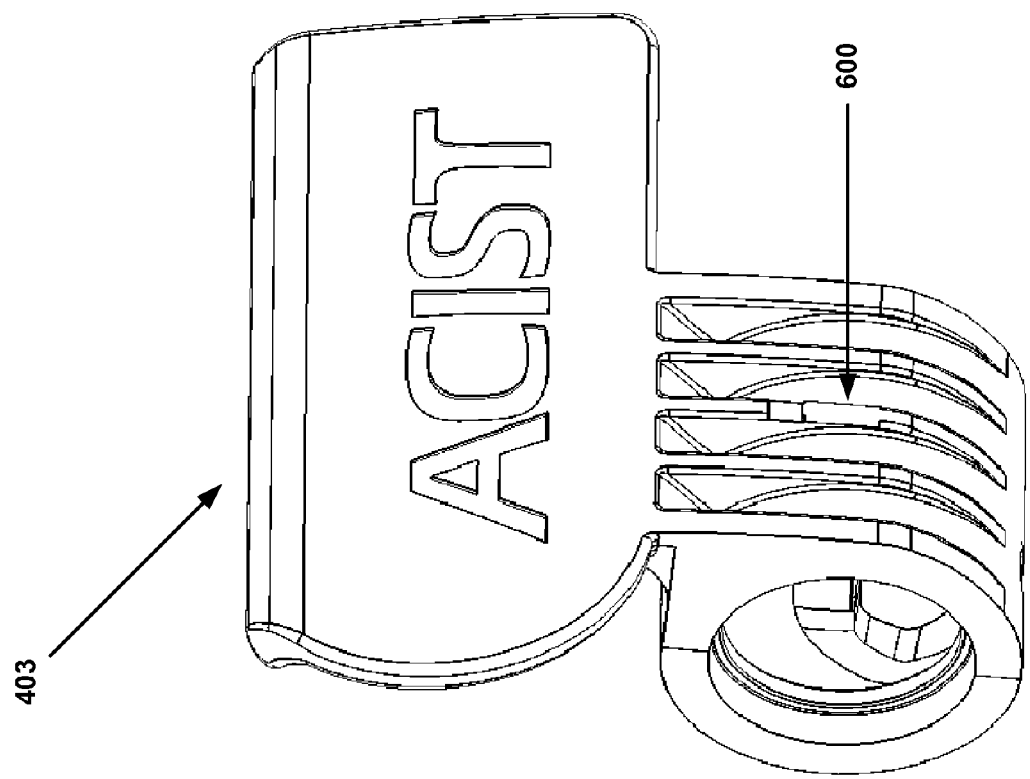
Figure 7B:
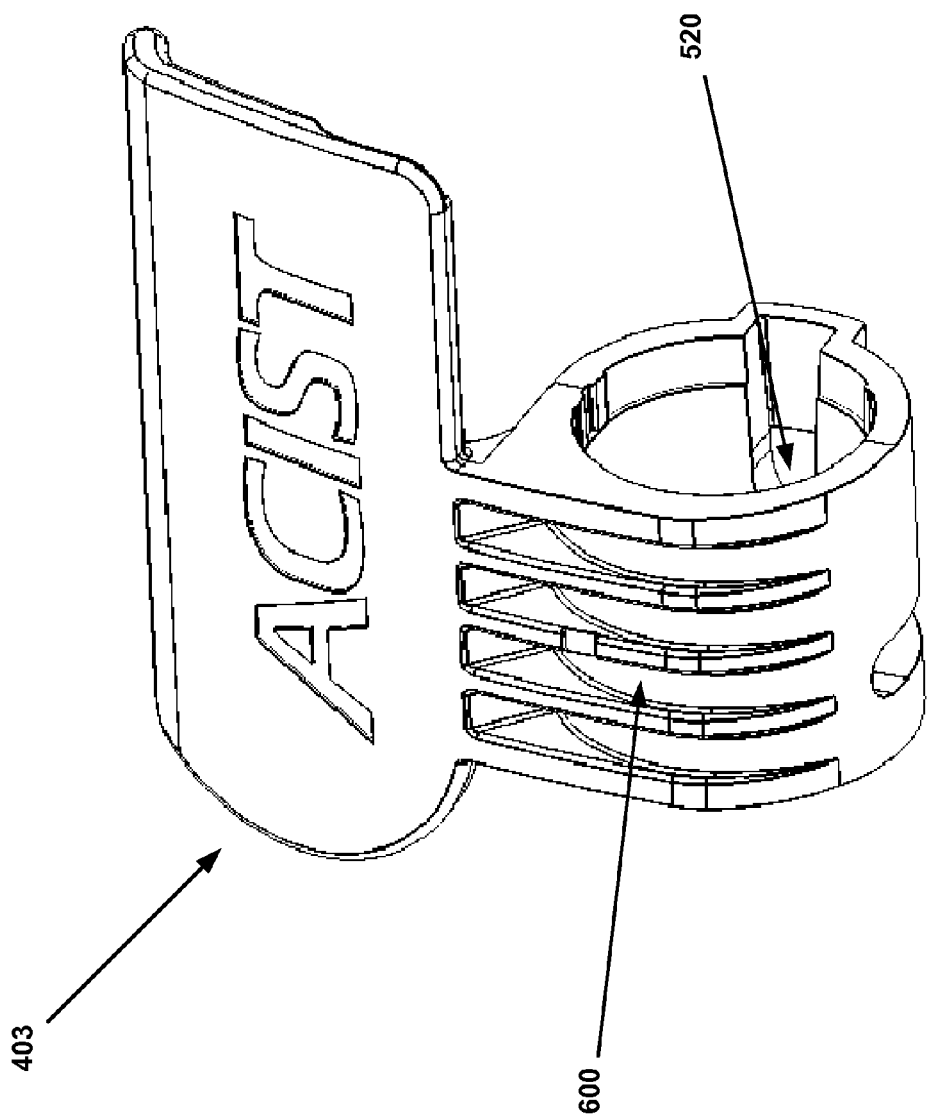

In one embodiment, lever 403 may includes a plurality of ribs, as shown more clearly in FIGS. 7A-7B. In some cases, at least one of fluid connectors 402 and 404 includes at least one transparent end connector. For example, one or both of end connectors 508 and 512 may comprise transparent connectors.

In one embodiment, a portion of at least one of fluid connectors 402 and 404 may be made of an overmolded, thermoplastic elastomer. For example, tube connectors 506 and 510 may be made of an overmolded, thermoplastic elastomer. In some cases, upon connection of assembly 401 to device 200, and upon locking of the lever 403 to guide rod 220, tube connectors 506 and 510 may be inserted into and between air detectors 236A and 236B, respectively. In these cases, device 200 may utilize air detectors 236A and 236B to determine if air may be present in tube connectors 506 and/or 510. For example, air detectors 236A and 236B may comprise acoustic detectors that are capable of determining whether air bubbles or columns may be present in tube connectors 506 and/or 510.

Thus, device 200 is capable of detecting air within assembly 401, which may comprise a disposable component, after it has been connected to device 200. The use of air detectors 236A and/or 236B may help identify any air that is present well downstream of the pressurizing units that are loaded into sleeves 216A and 216B. Thus, any air that may be present in tubing connected to these pressurizing units and that is also connected to tube connector 506 and/or 510 may be detected by air detectors 236A and/or 236B.

In some instances, an operator may wish to connect assembly 401 to device 200 within a sterile field during a patient injection procedure. In these instances, device 200 may be a non-sterile component, while assembly 401 may be a sterilized, disposable component that is to be used during the patient injection procedure and subsequently discarded. (One or more portions of device 200 may be covered with a sterile drape.) So that the operator may maintain sterility within the sterile field, the operator may be able to connect assembly 401 to device 200 using a one-handed operation.

For example, the operator may be use one hand to hold assembly 401 near guide rod 220 of device 200, and then cause guide rod 220 to be inserted into guide rod channel 540 of assembly 401, such that fluid connectors 402 and 404 move towards and corresponding fluid connectors on device 200 for connection. Subsequently, the operator may use one or more fingers of the operator's hand to rotate lever 403 (e.g., up) into a locked position, causing a portion of guide rod 220 to be locked into locking groove 520. At this point, the operator could initiate an injection procedure. Upon completion of the procedure, the operator may use one or more fingers to rotate lever 403 (e.g., back down) into an unlocked position, such that assembly 401 may be removed by device 200 via guide rod 220. The assembly 401 (which may be part of patient line 400 shown in FIG. 4) may then be discarded.

Figure 6:
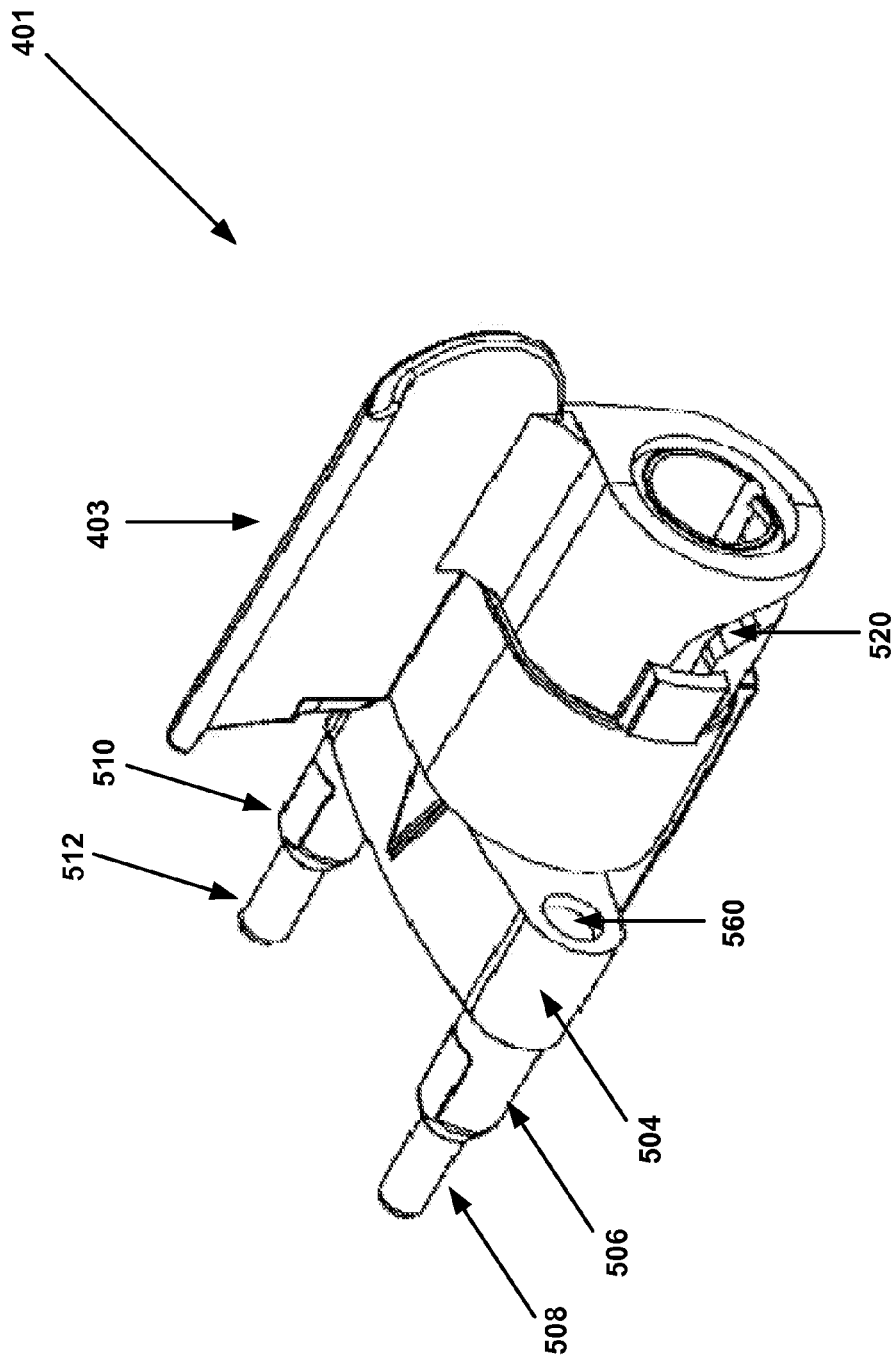
FIG. 6 is a perspective diagram of certain components of the fluid connection assembly shown in FIGS. 5A-5D, where a locking mechanism has been moved into a different position, according to one embodiment.

FIG. 6 is a perspective diagram of certain components of fluid connection assembly 401 shown in FIGS. 5A-5D, where a locking mechanism has been moved into a different position, according to one embodiment. As shown in the example of FIG. 6, lever 403 has been rotated into an upright position, such that lever 403 lies alone a plane that is substantially normal to a plane defined by housing member 504. For example, an operator may use a one-handed manual operation to move lever 403 into the upright position that is shown in FIG. 6. In this particular example, lever 403, which is part of the locking mechanism of assembly 401, has been moved into the locked position, such that pin 223 of rod 220 may, when engaged with assembly 401, become locked within locking groove 520 as lever 403 is rotated from the unlocked position into the locked position.

FIG. 6 also shows another tube channel 560 in assembly 401. Tube channel 560 runs through housing member 504. Fluid tubing 406 (FIGS. 5A-5D) may run through tube channel 560 and connect with fluid connector 402.

FIGS. 7A-7C are perspective diagrams more detailed views of lever 403 included in fluid connection assembly 401 shown in FIGS. 5A-5D, according to one embodiment. FIGS. 7A and 7B show that lever 403 includes a plurality of ribs 600 in this embodiment. Fluid connection assembly 401 may, in some cases, be manufactured using an injection molding process. By including ribs 600 in these cases, fluid connection assembly 401 may be molded with fairly uniform thicknesses throughout (e.g., no thick volumes).

FIG. 7C also shows a more detailed view of locking groove 520, as FIG. 7C is a perspective diagram of the underside of lever 403. As can be understood from review of FIG. 7C, pin 223 of guide rod 220 (FIG. 2E) may become engaged, or locked, within groove 520 when lever 403 is rotated from a first position to a second position. Typically, an operator would insert guide rod 220 of device 200 within guide rod channel 540 of assembly 401 until pin 223 of guide rod 220 is placed in proximity to channel 520.

For example, the operator may move assembly 401 over guide rod 220 until pin 223 is located at one end of channel 520. Lever 403 may be in an unlocked position at this point. The operator may then move, or rotate, lever 403 into a locked position, such that pin 223 moves into and becomes fully engaged, or locked, within groove 520. Once lever 403 has been moved into the locked position, assembly 401 may become affirmatively coupled to guide rod 220, as pin 223 of guide rod 220 has become locked within groove 520. Subsequently, the operator may rotate lever 403 back into an unlocked position, such that pin 223 becomes disengaged from groove 520. At this point, assembly 401 may be removably decoupled from guide rod 220, so that the operator may slide assembly 401 off guide rod 220 to remove it from device 200.

Figure 8:
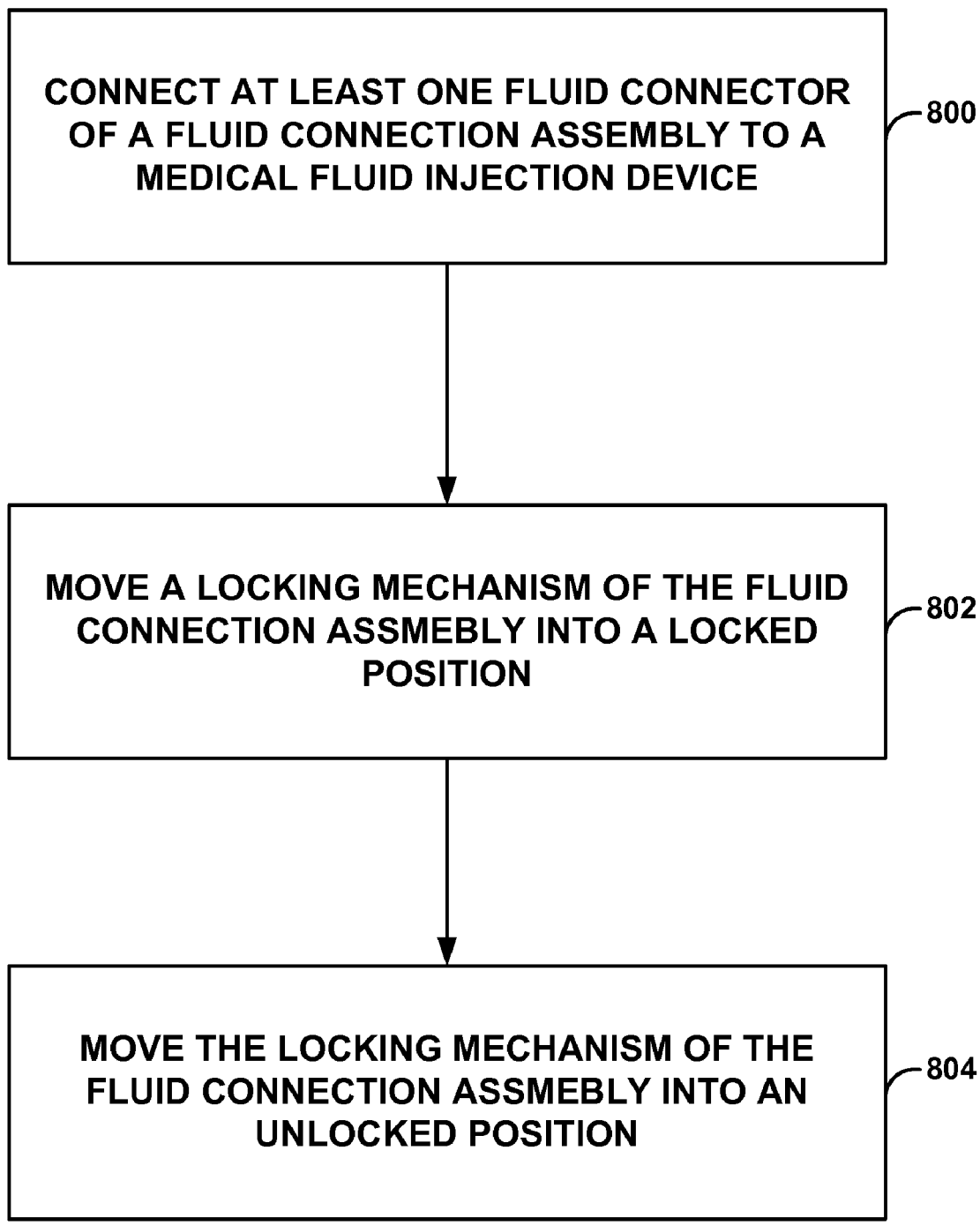
FIG. 8 is a flow diagram of a method that may be performed to connect the fluid connection assembly shown in FIGS. 5A-5D to a powered medical fluid injection device, according to one embodiment.

FIG. 8 is a flow diagram of a method that may be performed to connect fluid connection assembly 401, shown in FIGS. 5A-5D, to a powered medical fluid injection device, such as device 100 (FIGS. 1A-1B) and/or device 200 (FIGS. 2A-2E), according to one embodiment. For purposes of illustration only, it will be assumed in the following description that the method shown in FIG. 8 is performed to connect fluid connection assembly 401 to device 200.

Initially, at least one fluid connector (e.g., fluid connector 402 and/or 404) of a fluid connection assembly (e.g., fluid connection assembly 401) may be connected to a medical fluid injection device (e.g., device 200) (800). For example, an operator, such as a clinician, may connect the at least one fluid connector to the device (e.g., such as to connector 306, shown in FIG. 3, of device 200). In one embodiment, a high-pressure seal is created between the at least one fluid connector and the medical fluid injection device.

A locking mechanism of the fluid connection assembly may be moved, e.g., rotated, into a locked position to affirmatively couple the fluid connection assembly to the medical fluid injection device (802). Upon use of the fluid connection assembly, the locking mechanism of the fluid connection assembly may be moved, e.g., rotated, into an unlocked position to removably decouple the fluid connection assembly from the medical fluid injection device (804). In some cases, an operator may use a one-handed operation to manually move, or rotate, the locking mechanism into either the locked or unlocked position.

In some instances, connecting the at least one fluid connector to the medical fluid injection device may include receiving a guide rod (e.g., guide rod 220 shown in FIGS. 2A-2C and 2E) of the medical fluid injection device within a guide-rod channel (e.g., guide rod channel 540 shown in FIG. 5D). In these instances, the locking mechanism may be moved into the locked position to affirmatively couple the locking mechanism to the guide rod. The locking mechanism may be moved into the unlocked position to removably decouple the locking mechanism from the guide rod. The guide rod may be received within the guide-rod channel to permit alignment of the at least one fluid connector with at least one corresponding connector of the medical fluid injection device.

The locking mechanism may include a locking groove (e.g., locking groove 520 shown in FIG. 5B). A portion of the guide rod may be locked within the locking groove to restrict movement of the fluid connection assembly on the guide rod when the locking mechanism is moved into the locked position. When the locking mechanism is moved into the unlocked position, the portion of the guide rod may be unlocked within the locking groove to permit movement of the fluid connection assembly on the guide rod.

In one embodiment, moving the locking mechanism into the locked position may include positioning a lever (e.g., lever 403) along a first plane that is substantially normal to a plane defined by at least one housing member (e.g., housing member 502 and/or 504) of the fluid connection assembly. Moving the locking mechanism into the unlocked position may include positioning the lever along a second plane that is substantially co-planar with the plane defined by the at least one housing member. In some instances, an operator may manually move the locking mechanism into either the locked or unlocked position using a one-handed operation.

In some cases, fluid tubing (e.g., tubing 406 and/or 408) may be connected to the fluid connection assembly, such as by an operator. Upon moving the locking mechanism into the locked position, the method may further include injecting medical fluid from the medical fluid injection device into the fluid connection assembly and the fluid tubing. For example, device 200 may inject fluid from a pressurizing unit within sleeve 216A or 216B into the fluid connection assembly and tubing.

Subsequent to injecting the medical fluid, the method may further include moving the locking mechanism into the unlocked position (e.g., such as by a user). Upon moving the locking mechanism into the unlocked position, the fluid connection assembly may be removed from the medical fluid injection device.

In one embodiment, the at least one fluid connector includes a sterilized component and the medical fluid injection device comprises a non-sterilized component. In this embodiment, an operator may be able to use a one-handed manual operation to connect the at least one fluid connector to the medical fluid injection device while maintaining a sterility of the at least one fluid connector.

In one embodiment, a portion of the at least one fluid connector may be inserted into an air detector (e.g., air detector 236A or 236B shown in FIG. 2D) of the medical fluid injection device. The air detector may determine whether or not an amount of air is present in the portion of the at least one fluid connector. If air is present, the device may alert the operator, such that the air may be purged from the portion of the at least one fluid connector. In some instances, the operator may terminate an injection procedure, or remove the fluid connection assembly from the device if air is detected in the portion of the at least one fluid connector.

Various embodiments have been described herein. These and other embodiments are within the scope of the following claims.

The invention claimed is:

1. A fluid connection assembly, comprising:
   at least one fluid connector;
   a mating mechanism coupled to the at least one fluid connector and configured to connect the at least one fluid connector to a powered medical fluid injection device that is external to the fluid connection assembly, wherein the mating mechanism comprises a guide-rod channel that is configured to receive a guide rod of the powered medical fluid injection device when connecting the at least one fluid connector to the powered medical fluid injection device; and
   a locking mechanism coupled to the mating mechanism and rotatable into a locked position or an unlocked position,
   wherein the locking mechanism becomes affirmatively coupled to the guide rod of the powered medical fluid injection device when the locking mechanism is rotated into the locked position, such that fluid may be injected from the powered medical fluid injection device into the fluid connection assembly via the at least one fluid connector, and
   wherein the locking mechanism becomes removably decoupled from the guide rod of the powered medical fluid injection device when the locking mechanism is rotated into the unlocked position.

2. The fluid connection assembly of claim 1, wherein:
   the at least one fluid connector comprises a plurality of fluid connectors; and
   the mating mechanism comprises at least one housing member that is coupled to the fluid connectors.

3. The fluid connection assembly of claim 1, wherein:
   the locking mechanism comprises a locking groove;
   the locking mechanism is in the locked position when a portion of the guide rod is locked within the locking groove to restrict movement of the fluid connection assembly on the guide rod; and
   the locking mechanism is in the unlocked position when the portion of the guide rod is unlocked within the locking groove to permit movement of the fluid connection assembly on the guide rod.

4. The fluid connection assembly of claim 1, wherein the guide-rod channel is configured to receive the guide rod to permit alignment of the at least one fluid connector with at least one corresponding connector of the medical fluid injection device.

5. The fluid connection assembly of claim 1, wherein the locking mechanism comprises a lever.

6. The fluid connection assembly of claim 5, wherein:
   the locking mechanism is in the locked position when the lever is positioned along a first plane that is substantially normal to a plane defined by at least one housing member of the fluid connection assembly; and
   the locking mechanism is in the unlocked position when the lever is positioned along a second plane that is substantially co-planar with the plane defined by the at least one housing member.

7. The fluid connection assembly of claim 5, wherein the lever comprises a plurality of ribs.

8. The fluid connection assembly of claim 1, wherein the at least one fluid connector comprises at least one transparent end connector.

9. The fluid connection assembly of claim 1, wherein the fluid connection assembly comprises a disposable, sterilized assembly.

10. The fluid connection assembly of claim 1, further comprising fluid tubing that is coupled to the at least one fluid connector.

11. A method comprising:
    connecting at least one fluid connector of a fluid connection assembly to a powered medical fluid injection device that is external to the fluid connection assembly, wherein a guide-rod channel of the fluid connection assembly receives a guide rod of the powered medical fluid injection device;
    rotating a locking mechanism of the fluid connection assembly into a locked position to affirmatively couple the locking mechanism with the guide rod of the powered medical fluid injection device, such that fluid may be injected from the powered medical fluid injection device into the fluid connection assembly via the at least one fluid connector; and
    upon use of the fluid connection assembly, rotating the locking mechanism of the fluid connection assembly into an unlocked position to removably decouple the locking mechanism from the guide rod of the powered medical fluid injection device.

12. The method of claim 11, wherein the locking mechanism comprises a locking groove, and wherein:
    rotating the locking mechanism into the locked position comprises locking a portion of the guide rod within the locking groove to restrict movement of the fluid connection assembly on the guide rod; and
    rotating the locking mechanism into the unlocked position comprises unlocking the portion of the guide rod within the locking groove to permit movement of the fluid connection assembly on the guide rod.

13. The method of claim 11, wherein receiving the guide rod of the medical fluid injection device within the guide-rod channel comprises receiving the guide rod within the guide-rod channel to permit alignment of the at least one fluid connector with at least one corresponding connector of the medical fluid injection device.

14. The method of claim 11, wherein:
    rotating the locking mechanism into the locked position comprises positioning a lever along a first plane that is substantially normal to a plane defined by at least one housing member of the fluid connection assembly; and
    rotating the locking mechanism into the unlocked position comprises positioning the lever along a second plane that is substantially co-planar with the plane defined by the at least one housing member.

15. The method of claim 11, further comprising:
connecting fluid tubing to the fluid connection assembly; and
upon rotating the locking mechanism into the locked position, injecting medical fluid from the medical fluid injection device into the fluid connection assembly and the fluid tubing.

16. The method of claim 15, wherein the method comprises rotating the locking mechanism into the unlocked position subsequent to injecting the medical fluid, and wherein the method further comprises:
upon rotating the locking mechanism into the unlocked position, removing the fluid connection assembly from the medical fluid injection device.

17. The method of claim 11, wherein the at least one fluid connector comprises a sterilized component, wherein the medical fluid injection device comprises a non-sterilized component, and wherein connecting the at least one fluid connector to the medical fluid injection device occurs while maintaining a sterility of the at least one fluid connector.

18. The method of claim 11, wherein connecting the at least one fluid connector to the medical fluid injection device comprises inserting a portion of the at least one fluid connector into an air detector of the medical fluid injection device.

19. The method of claim 18, further comprising:
using the air detector to determine whether or not an amount of air is present in the portion of the at least one fluid connector.

20. The method of claim 11, wherein connecting the at least one fluid connector to the medical fluid injection device comprises connecting the at least one fluid connector to the medical fluid injection device using a one-handed manual operation.

21. The method of claim 11, wherein connecting the at least one fluid connector to the medical fluid injection device comprises creating a high-pressure seal between the at least one fluid connector and the medical fluid injection device.

* * * * *